US008815517B2

(12) United States Patent
Keene et al.

(10) Patent No.: US 8,815,517 B2
(45) Date of Patent: Aug. 26, 2014

(54) METHODS FOR IDENTIFYING FUNCTIONALLY RELATED GENES AND DRUG TARGETS

(75) Inventors: Jack D. Keene, Durham, NC (US); Scott A. Tenenbaum, Durham, NC (US); Craig C. Carson, Raleigh, NC (US); William C. Phelps, Durham, NC (US)

(73) Assignee: Ribonomics, Inc., Woburn, MA (US)

( * ) Notice: Subject to any disclaimer, the term of this patent is extended or adjusted under 35 U.S.C. 154(b) by 110 days.

(21) Appl. No.: 10/309,788

(22) Filed: Dec. 4, 2002

(65) Prior Publication Data
US 2003/0211466 A1 Nov. 13, 2003

Related U.S. Application Data

(63) Continuation-in-part of application No. 09/750,401, filed on Dec. 28, 2000, now Pat. No. 6,635,422.

(60) Provisional application No. 60/173,338, filed on Dec. 28, 1999.

(51) Int. Cl.
*C12Q 1/68* (2006.01)
*C12N 15/09* (2006.01)
*C07K 17/04* (2006.01)
*C07K 19/00* (2006.01)
*C12N 15/07* (2006.01)
*C12N 15/11* (2006.01)

(52) U.S. Cl.
USPC ......... 435/6.13; 435/6.19; 435/7.1; 435/7.23; 435/455; 435/91.51; 530/300; 530/350; 530/344; 530/412; 536/23.1; 536/25.4

(58) Field of Classification Search
CPC .......... C12Q 1/00; C12Q 1/68; C12Q 1/6883; C12Q 1/6886; C12Q 2522/101; C07H 21/00; C07K 14/4713
See application file for complete search history.

(56) References Cited

U.S. PATENT DOCUMENTS

| | | | |
|---|---|---|---|
| 5,444,149 A | 8/1995 | Keene et al. | 530/300 |
| 5,525,495 A | 6/1996 | Keene et al. | 435/172.3 |
| 5,541,291 A | 7/1996 | Keene | 530/350 |
| 5,561,222 A | 10/1996 | Keene et al. | 530/350 |
| 5,583,016 A | 12/1996 | Villeponteau et al. | |
| 5,773,246 A | 6/1998 | Keene et al. | 435/69.1 |
| 5,807,707 A | 9/1998 | Andrews et al. | |
| 5,859,227 A | 1/1999 | Giordano et al. | |
| 5,866,680 A | 2/1999 | Keene et al. | 530/324 |
| 5,882,866 A | 3/1999 | Keene | 435/6 |
| 5,955,299 A | 9/1999 | Hillman et al. | |
| 5,972,620 A | 10/1999 | Keene | 435/6 |
| 6,166,192 A | 12/2000 | Spiegelman et al. | |
| 6,326,150 B1 | 12/2001 | Golemis et al. | |
| 6,458,559 B1 | 10/2002 | Shi et al. | |
| 6,631,211 B1 | 10/2003 | Schermer et al. | |
| 6,635,422 B2 | 10/2003 | Keene et al. | |
| 7,504,210 B2 | 3/2009 | Keene et al. | |
| 2002/0004211 A1 | 1/2002 | Keene et al. | 435/7.21 |
| 2002/0127619 A1* | 9/2002 | Jett et al. | 435/7.23 |
| 2003/0211466 A1 | 11/2003 | Keene et al. | |
| 2003/0235830 A1 | 12/2003 | Keene et al. | |
| 2004/0096878 A1 | 5/2004 | Keene et al. | |
| 2006/0147980 A1 | 7/2006 | Keene et al. | |
| 2006/0257857 A1 | 11/2006 | Keene et al. | |
| 2008/0113362 A1 | 5/2008 | Keene et al. | |
| 2008/0206763 A1 | 8/2008 | Keene et al. | |
| 2008/0248479 A1 | 10/2008 | Keene et al. | |
| 2008/0254461 A1 | 10/2008 | Keene et al. | |
| 2009/0081651 A1 | 3/2009 | Keene et al. | |

FOREIGN PATENT DOCUMENTS

| | | | |
|---|---|---|---|
| WO | WO 94/06934 | 3/1994 | ............... C12Q 1/68 |
| WO | WO9837422 | 8/1998 | |
| WO | WO-01/48480 | 7/2001 | |

OTHER PUBLICATIONS

Eckstein, ISOA/ARF Drug Development, Alzheimer Research Forum, pp. 1-18.*
Orth et al, The promise of genomics to identify novel therapeutic targets, Expert Opinions Ther Targets, 2004, pp. 587-596.*
Tenenbaum, Ribonomics: identifying mRNA subsets in mRNP compelxes using antibodies to RNA-binding proteins and genomic arrays, Methods, 2002, vol. 26, pp. 191-198.*
Tenenbaum et al, Identifying mRNA subsets in messenger ribonucleoprotein complexes by using cDNA arrays, PNAS, 2000, vol. 97, pp. 14085-14090.*
Ceman et al, Isoaltion of an FMRP-Associated Messenger Ribonucleoprotein Particle and Identification of Nucleolin and the Fragile X-Related Proteins as Components of the Complex, MCB, 1999, vol. 19(12) pp. 7925-7932.*
Dobashi et al, Expression of HuD Protein is Essential for Initial Phase of Neuronal Differentiation in Rat Pheochromocytoma PC12 Cells, BBRC, 1998. Vp; 244, p. 226-229.*
Ciesla, J. Metabolic enzymes that bind RNA: yet another level of cellular regulatory network? Acta Biochimica Polonica, Paper in Presss, No. 1211. downloaded Feb. 21, 2006.*
Stein et al, Stabilization of Vascular Endothelial Growth Factor mRNA by Hypoxia and Hypoglycemia and Coregulation with Other Ischemia-Induced Genes, MCB, 1995, vol. 15 (10) pp. 5365-5368.*
Eckstein, ISONARF Drug Development, Alzheimer Research Forum, pp. 1-18, downloaded Feb. 20, 2006.*
Brown et al., Nov. 16, 2001, "Microarray Identification of FMRP-Associated Brain mRNAs and Altered mRNA Translational Profiles in Fragile X Snydrome", vol. 107:4, pp. 477-487.
Cheatham et al., Dec. 2, 2002, "A Ribonomic Analysis of Adipocytes: A Systems Biology Tool", Retrieved from the Internet: URL:http://www.ribonomics.com/news/presentations/ribonomics_MetabolicDisease2002Poster.pdf>.

(Continued)

*Primary Examiner* — Maria Marvich
(74) *Attorney, Agent, or Firm* — Foley Hoag LLP

(57) ABSTRACT

The identification and evaluation of mRNA and protein targets associated with mRNP complexes and implicated in the expression of proteins involved in common physiological pathways is described. Effective targets are useful for treating a disease, condition or disorder associated with the physiological pathway.

28 Claims, 16 Drawing Sheets

(56) References Cited

OTHER PUBLICATIONS

Gavin et al., Jan. 2002,"Functional Organization of the Yeast Proteome by Systematic Analysis of Protein Complexes", Nature, MacMillan Journals Ltd., vol. 415, pp. 141-147.
Herold et al., May 15, 2003, "Genome-Wide Analysis of Nuclear mRNA Export Pathways in *Drosophila*", vol. 22:10, pp. 2472-2483.
Hieronymus et al., Feb. 2003, "Genome-Wide Analysis of RNA-Protein Interactions Illustrates Specificity of the mRNA export Machinery", vol. 33:2, pp. 155-161.
Keene et al., Jun. 19, 2001, Ribonucleoprotein Infrastructure Regulating the Flow of Genetic Information Between the Genome and the Proteome, vol. 98:13, pp. 7018-7024.
Keene et al., Jun. 2002, "Eukaryotic mRNPs May Represent Post-transcriptional Operons", vol. 9:6, pp. 1161-1167.
Knoch Klaus-Peter et al., Mar. 3, 2004, "Polypyrimidine Tract-Binding Protein Promotes Insulin Secretory Granule Biogenesis", vol. 6:3, pp. 207-214.
Lelivelt et al., Oct. 1999, "Yeast Upf Proteins Required for RNA Surveillance Affect Global Expression of the Yeast Transcriptome", vol. 19:10, pp. 6710-6719.
Ohashi et al., Oct. 4, 2002, "Identification of mRNA/Protein (mRNP) Complexes Containing Purα, mStaufen, Fragile X Protein, and Myosin Va and their Association with Rough Endoplasmic Reticulum Equipped with a Kinesin Motor", The Journal of Bio. Chem., vol. 277:40, pp. 37804-37810.
Phelps, W.B., Nov. 6, 2002, "Innovative Systems Biology", Online, Retrieved from Internet: URL:http://www.ribonomics.com/news/presentations/ribonomics_RNA_in Drug_Devlopment.
Ribonomics, Inc., Mar. 17, 2003, "Research & Technology", Retrieved from the Internet: URL:http://web.archive.org/web/20030317064208/http://www.ribonomics.com/technology/index.html>.
Rodgers et al., Feb. 2002, "Identifying mRNAs bound by RNA-Binding Proteins Using Affinity Purification and Differential Display", vol. 26:2, pp. 115-122.
Tillmar et al., Jan. 11, 2002, "Control of Insulin mRNA Stability in Rat Pancreatic Islets", The Journal of Biological Chemistry, vol. 277:2, pp. 1099-1106.
Chen et al., "RNA-Protein Interactions: Involvement of NS3, NS5, and 3' Noncoding Regions of Japanese Encephalitis Virus Genomic RNA," Journal of Virology, vol. 17, No. 5, pp. 3466-3473, May 1997.
Tamanini et al. "Oligomerization Properties of Fragile-X Mental-Retardation Proetein (FMRP) and the Fragile-X-Related Proteins FXR1P and FXR2P," Biochem., vol. 343, pp. 517-523, 1999.
Tillmar et al., "Hypoxia May Increase Rat Insulin mRNA Levels by Promoting Binding of the Polypyrimidine Tract-Binding Protein (PTB) to the Pyrimidine-Rich Insulin mRNA-3'-Untranslated Region," Molecular Medicine, 8(5), pp. 263-272, 2002.
Wurtz et al., "Identification of Two RNA-Binding Proteins in Balbiani Ring Premessenger Ribonucleoprotein Granules and Presence of These Proteins in Specific Subsets of Heterogeneous Nuclear Ribonucleoprotein Particles," Molecular and Cellular Biology, vol. 16, No. 4, pp. 1425-1435, Apr. 1996.
Ashley, Jr. et al., "FMR1 Protein: Conserved RNP Family Domains and Selective RNA Binding", this is from (1993) Science 262:563-566.
DeMaria et al., "AUF1 Binding Affinity to A+U-rich Elements Correlates with Rapid mRNA Degradation", J. of Bio. Chem., vol. 271, No. 21, pp. 12179-12184 (1996).
Görlach et al., "The Determinants of RNA-Binding Specificity of the Heterogeneous Nuclear Ribonucleoprotein C Proteins", J. of Bio. Chem., vol. 269, No. 37, pp. 23074-23078 (1994).
Görlach et al., "The mRNA Poly(A)-Binding Protein: Localization, Abundance, and RNA-Binding Specificity", Exper. Cell Research, vol. 211, Issue 2, (1994).
Ma et al., "Cloning and Characertization of HuR, a Ubiquitously Expressed Elav-Like Protein", J. of Bio. Chem., vol. 271, No. 14, pp. 8144-8151, (1996).

Pérez et al., "Multiple RRMs Contribute to RNA Binding Specificity and Affinity for Polypyrimidine Tract Binding Protein", Biochemistry, 36, pp. 11881-11890 (1997).
Wei et al., "Wheat Germ Poly(A) Binding Protein Enhances the Binding Affinity of Eukaryotic Initiation Factor 4F and (iso)4F for Cap Analogues", Biochemistry, 37, pp. 1910-1916, 1998.
Ashley, Jr. et al.; "FMRI Protein: Conserved RNP Family Domains and Selective RNA Binding"; Science; 262:563-566 (1993).
Bachler et al.; StreptoTag: A Novel Method for the Isolation of RNA-Binding Proteins; RNA Journal; 5:1509-1516 (1999).
Beach et al.; Ribotrap: Targeted Purification of RNA-Specific RNPs from Cell Lysates Through Immunoaffinity Precipitation to Identify Regulatory Proteins and RNAs; Methods in Molecular Biology; 419:69-91; Post-Transcriptional Gene Regulation; Humana Press; Totowa, NJ USA (2008).
Harper et al.; RNA Binding Specificity of a *Drosophila* snRNP Protein that Shares Sequence Homology with Mammalian U1-A and U2-B Proteins, Nucleic Acids Research; vol. 20, No. 14, pp. 3645-3650 (1992).
Jansen, R.P.; RNA-Cytoskeletal Associations; FASEB J.; 13:455-466 (1999).
Lazarova et al.; HuD, A Neuronal-Specific RNA-Binding Protein, Is a Putative Regulator of N-myc Pre-mRNA Processing/Stability in Malignant Human Neuroblasts, Oncogene 18:2703-2710 (1999).
Monsalve et al.; Direct Coupling of Transcription and mRNA Processing through the Thermogenic Coactivator PGC-1; Molecular Cell; 6:307-316 (2000).
Sbicego et al.; RBP38, a Novel RNA-Binding Protein from Trypanosomatid Mitochondria, Modulates RNA Stability; Eukaryotic Cell; p. 560-568 (Jun. 2003).
Sengupta et al.; Identification of RNAs That Bind to a Specific Protein Using the Yeast Three-Hybrid System; RNA; 5:596-601 (1999).
Svitkin et al.; General RNA Binding Proteins Render Translation Cap Dependent; The EMBO Journal; vol. 15 (24); pp. 7147-7155 (1996).
Tsai et al.; In Vitro Section of an RNA Epitope Immunologically Cross-Reactive with a Peptide; Proc. National Academy of Sciences; 89:8864-8868 (1992).
Vasudevan et al.; AU-Rich-Element-Mediated Upregulation of Translation by FXR1 and Argonaute 2; Cell 128; pp. 1105-1118 (Mar. 23, 2007).
Wilson et al.; Functional Requirements for Specific Ligand Recognition by a Biotin-Binding RNA Pseudoknot, Biochemistry; 37:14410-14419 (1998).
Yang et al., Mouse Testis Brain RNA-Binding Protein/Translin Selectively Binds to the Messenger RNA of the Fibrous Sheath Protein Glyceraldedyde 3-Phosphate Dehydrogenase-S and Suppresses Its Translation In Vitro, Biology of Reproduction 68, 853-859 (2003).
Zhao et al.; TRAP-ing The Ribonome: A Novel Method for Isolating RNPs and Studying RNA-Protein Interactions; CytoStore; Technical Bulletin #G0601; www.cytostore.com; pp. 1-9 (date unknown).
Allen et al., "Association of Guide RNA Binding Protein gBP21 with Active RNA Editing Complexes in *Trypanosoma brudei*," Molecular and Cellular Biology, 18:6014-6022 (1998).
Korman et al., "cDNA clones for the heavy chain of HLA-DR antigens obtained after immunopurification of polysomes by monoclonal antibody," Proc. Natl. Acad. Sci. USA, 79:1844-1848 (1982).
Lerner et al., "Antibodies to small nuclear RNAs complexed with proteins are produced by patients with systemic lupus erythematosus," Proc. Natl. Acad. Sci. USA, 76(11):5495-5499 (1979).
Takeda et al., "Human RNA Helicase A is a Lupus Autoantigen That is Cleaved During Apoptosis," The Journal of Immunology, 163:6269-6274 (1999).
Kastner, et al. "Structure of the Small Nuclear RNP Particle UI: Identification of the Two Structural Protuberances with RNP Antigens A and 70K," The Jounrnal of Cell Biology, 116(4): 839-849 (Feb. 1992).
Anderson, N.E., et al., "Autoimmune Pathogenesis of Paraneoplastic Neurological Syndromes," *CRC Critical Reviews in Neurobiology* vol. 3; pp. 245-299 (1987).

(56) References Cited

OTHER PUBLICATIONS

Antic, D., et al., "Embryonic Lethal Abnormal Visual RNA-binding Proteins Involved in Growth, Differentation, and Posttranscriptional Gene Expression," *American Journal of Human Genetics* vol. 61; pp. 273-278 (1997).

Antic, D., et al., "ELAV Tumor Antigen, Hel-N1, by Increases Translation of Neurofilament M mRNA and Induces Formation of Neurites in Human Teratocarcinoma Cells," *Genes & Development* vol. 13; pp. 449-461 (1999).

Atasoy, U., et al., "ELAV Protein HuA (HuR) can Redistribute Between the Nucleus and Cytoplasm and is Unregulated During Serum Stimulation and T Cell Activation," *Journal of Cell Science* vol. 111; pp. 3145-3156 (1998).

Ceman et al., "Isolation of an FMRP-Associated Messenger Ribonucleoprotein Particle and Identification of Nucleolin and the Fragile X-Related Proteins as Components of the Complex," *Molecular and Cellular Biology*, 19(12):7925-7932 (1999).

Chambers, J.C., et al., "Isolation and Analysis of cDNA Clones Expressing Human Lupus La Antigen," *Proc. Natl. Acad. Sci. USA* vol. 82; pp. 2115-2119 (1985).

Crino, P., et al., "Presence and Phosphorylation of Transcription Factors in Developing Dendrites," *Proc. Natl. Acad. Sci. USA* vol. 95; pp. 2313-2318 (1998).

Dalmau, J., et al., "The Expression of the Hu Antigen in Human Normal and Tumor Tissues," *American Journal of Pathology* vol. 141; pp. 881-886 (1999).

Duggan, D.J., et al., "Expression Profiling using cDNA Microarrays," *Nature Genetics* vol. 21; pp. 10-14 (1999).

Fan, X.C., et al., "Overexpression of HuR, a Nuclear-Cytoplasmic Shuttling Protein, Increases the in vivo Stability of ARE-Containing mRNAs," *The EMBO Journal* vol. 17; pp. 3448-3460 (1998).

Gao, F.B., et al., "Hel-N1/Hel-N2 Proteins are Bound to PolyA + mRNA in Granular RNP Structures and are Implicated in Neuronal Differentiation," *Journal of Cell Science* vol. 109, pp. 579-589 (1995).

Gao, F., et al., "Selection of a Subset of mRNAs from 3'UTR Combinatorial Libraries Using Neuronal RNA-Binding Protein, Hel-N1," *Proc. Natl. Acad. Sci. USA* vol. 91; pp. 11207-11211 (1994).

Good, P.J., "A Conserved Family of Elav-Like Genes in Vertebrates," *Proc. Nat. Acad. Sci.* vol. 92; pp. 4557-4561 (1995).

Jain, R.G., et al., "Ectopic Expression of Hel-N1, and RNA-Binding Protein, Increases Glucose Transporter (GLUT1) Expression in 3T3-L1 Adipocytes," *Molecular and Cellular Biology* vol. 17; pp. 954-962 (1997).

Keene, J.D., "Combinatorial Chemistry: Randomization and Selection of RNA to Identify Targets for RRM RNA-Binding Proteins and Antibodies," *Methods in Enzymology*, J.E. Dahlberg and J.N. Abelson, Eds., Academic Press, Inc. San Diego vol. 267; pp. 367-383 (1996).

Keene, J.D., "Methods and Compositions Useful in the Diagnosis and Treatment of Autoimmune Diseases," *Biotechnology Advances*, GB vol. 15; p. 525 Abstract (1997).

Keene, J.D., "Invited Commentary: Why is Hu Where? Shuttling of Early-Response Gene Messenger RNA Subsets," *Proc. Natl. Acad. Sci. USA* vol. 96; pp. 5-7 (1999).

Keene, J.D., "RNA Surfaces as Functional Mimetics of Proteins," *Chemistry & Biology* vol. 3; pp. 505-513, 1996.

King, P.H., et al., "Mammalian Homologs of *Drosphila* ELAV Localized to a Neuronal Subset can Bind in vitro to the 3' UTR of mRNA Encoding the Id Transcriptional Repressor," *Journal of Neuroscience* vol. 14; pp. 1943-1952 (1993).

Levine, T.D., et al., "Hel-N1: An Automimmune RNA-Binding Protein with Specificity for 3' Uridylate-Rich Untranslated Regions of Growth Factor mRNAs," *Molecular and Cellular Biology*, vol. 13; pp. 3494-3504 (1994).

Levy, N.S., et al., "Hypoxic Stabilization of Vascular Endothelial Growth Factor mRNA by the RNA-Binding Protein, HuR," *Journal of Biological Chemistry* vol. 273; pp. 6417-6423 (1998).

Loftus, S.K., et al., "Informatic Selection of a Neural Crest-Melanocyte cDNA set for Microarray Analysis," *Proc. Natl. Acad. Sci. USA* vol. 96; pp. 9277-9280 (1999).

Lutz-Freyermuth, C., et al., "The U1 RNA Binding Site of the U1 snRNP-Associated A Protein Suggests a Similarity with U2 snRNPs," *Molecular and Cellular Biology* vol. 9; pp. 2975-2982 (1989).

Peng, S., et al., "RNA Stabilization by the AU-Rich Element Binding Protein, HuR, an ELAV Protein," *The EMBO Journal J* vol. 17; pp. 3461-3470 (1998).

Perou, C.M., et al., "Distinctive Gene Expression Patterns in Human Mammary Epithelial Cells and Breast Cancers," *Proc. Natl. Acad. Sci. USA* vol. 96; pp. 9212-9217 (1999).

Richter, J.D., "Analysis of mRNA Formation and Function," *Academic Press*, San Diego, p. 237-261 (1997).

Schiavi, S.C., et al., "Regulation of Proto-Oncogene mRNA Stability," *Biochemical and Biophysical Acta* vol. 1114; pp. 95-106 (1992).

Sgroi, D.C., et al., "In Vivo Gene Expression Profile Analysis of Human Breast Cancer Progression," *Cancer Research* vol. 59; pp. 5656-5661 (1999).

Shimkets, et al., "Nature Biotechnology," vol. 17, 798-803 (1999).

Tenenbaum, S.A., et al., "Identifying mRNA Subsets in Messenger Ribonucleoprotein Complexes by using cDNA Arrays," *Proc. Natl. Acad. Sci. USA* vol. 97; pp. 14085-14090 (2000).

Tsai, D.E., et al., "U1snRNP—A Protein Selects a Ten Nucleotide Consensus Sequence from a Degenerate RNA Pool Presented in Various Structural Contexts," *Nucleic Acids Research* vol. 19; 4931-4936 (1991).

Tsai, D.E., et al., "In Vitro Selection of an RNA Epitope Immunologically Cross-Reactive with a Peptide," *Proc. Natl. Acad. Sci. USA* vol. 89; pp. 8864-8868 (1992).

Velculescu, V.E., et al., "Serial Analysis of Gene Expression," *Science* vol. 270; pp. 484-487 (1995).

Velculescu, V.E., et al., *Cell* vol. 88; pp. 243-251 (1997).

Wang, W., et al., "HuR Regulates Cyclin A and Cyclin B1 mRNA Stability During Cell Proliferation," *The EMBO Journal* vol. 19; pp. 1-12 (2000).

Wen, X., et al., "Large-Scale Temporal Gene Expression Mapping of Central Nervous System Development," *Proc. Natl. Sci. Acad. USA* vol. 95; 334-339 (1998).

Yang, G.P., et al, "Combining SSH and cDNA Microarrays for Rapid Identification of Differentially Expressed Genes," *Nucleic Acids Research* vol. 27; pp. 1517-1523 (1999).

Zhang, J., et al., "A Novel Cytoplasmic Protein with RNA-Binding Motifs is an Autoantigen in Human Hepatocellular Carcinoma," *Journal of Experimental Medicine* vol. 189; pp. 1101-1110 (1999).

Zhao, R., et al., "Analysis of p53-Regulated Gene Expression Patterns using Oligonucleotide Arrays," *Genes & Development* vol. 14; pp. 981-993 (2000).

Zong, Q., et al., "Messenger RNA Translation State: The Second Dimension of High-Throughput Expression Screening," *Proc. Natl. Acad. Sci. USA* vol. 96; pp. 10632-10636 (1999).

Buckanovich et al., "The Neuronal RNA Binding Protein Nova-1 Recognizes Specific RNA Targets In Vitro and In Vivo," *Molecular and Cellular Biology*, 17(6):3194-3201 (1997).

Reim et al., "The RRM Protein NonA From *Drosophila* Forms a Complex with the RRM Proteins Hrb87F and S5 and the Zn Finger Protein PEP on hnRNA," *Experimental Cell Research*, 253:573-586 (1999).

Chu et al., "Identification of a Thymidylate Synthase Ribonucleoprotein Complex in Human Cancer Cells," *Molecular and Cellular Biology*, 14(1):207-213 (1994).

\* cited by examiner

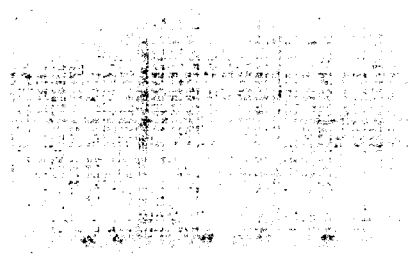
FIG. 6A Pre-bleed
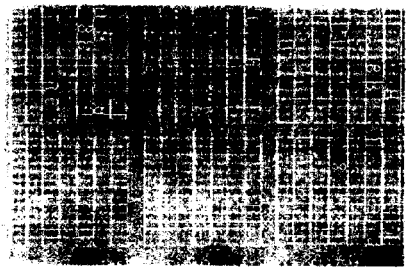
FIG. 6D PAPB mRNP    a b
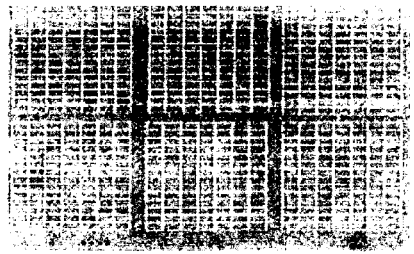
FIG. 6B HuB mRNP    a b
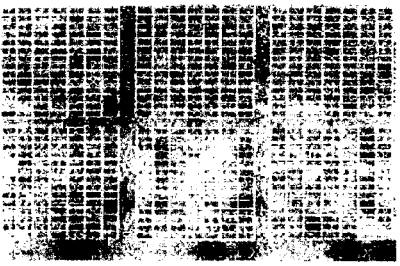
FIG. 6E Total RNA    a b
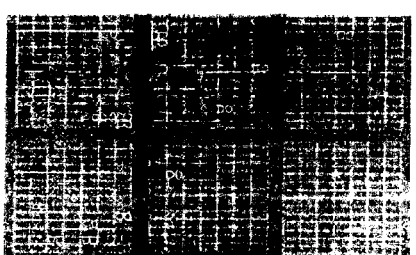
FIG. 6C eIF-4E mRNP    a b Untreated | RA Treated
HuB mRNP Complex HuA mRNP Complex Total Cellular RNA

METHODS FOR IDENTIFYING FUNCTIONALLY RELATED GENES AND DRUG TARGETS

RELATED APPLICATIONS

This application is a continuation-in-part of U.S. patent application Ser. No. 09/750,401, filed on Dec. 28, 2000, now U.S. Pat. No. 6,635,422, which claims the benefit of U.S. Provisional Application Ser. No. 60/173,338, filed Dec. 28, 1999, both of which are hereby incorporated by reference in their entirety.

GOVERNMENT SUPPORT

This invention was made with government support under grant number R01 CA79907 from the National Institutes of Health. The United States Government has certain rights in this invention.

FIELD OF THE INVENTION

The invention provides methods and compositions for identifying and characterizing functionally related gene products that are associated with mRNA-protein (mRNP) complexes and for characterizing cellular gene expression. The invention also provides methods and compositions for identifying and characterizing therapeutic targets and therapeutics.

BACKGROUND OF THE INVENTION

Most genes are regulated by a complex array of interactions, resulting in unique gene expression patterns. Such gene expression patterns vary between different cell types, cells at different developmental stages or differentiation states, and cells exposed to signaling molecules, stress, infection, or other cellular condition or disorder. Efforts to understand the processes that regulate variant gene expression patterns have concentrated on early events in transcription regulation and in events surrounding translation. In contrast, much less attention has been paid to the role of mRNA-protein complexes (mRNP complexes) in post-transcriptional regulatory processes, such as the regulation of stability, localization, and translation efficiency of mRNAs. Still less is known about the post-transcriptional processes that coordinate the expression of functionally related genes (e.g., genes that share or participate in a certain function or pathway), which are often co-localized to particular mRNP complexes and bound to the same RNA binding protein (RBP).

Post-transcriptional gene regulation of some mRNAs is mediated by regulatory elements or sequences that reside in both the introns and exons of pre-mRNAs, and the coding and noncoding regions of mature transcripts. One example of such a regulatory element is the AU-rich instability element (ARE) present in the 3'-untranslated regions (UTRs) of early-response gene mRNAs, many of which encode proteins essential for growth and differentiation. RNA binding proteins associated with mRNP complexes bind to AREs in vitro and mediate post-transcriptional mRNA stability and translation in vivo. However, not all mRNAs that bind to an RNA binding protein possess an ARE or other common regulatory element. Moreover, the mechanism(s) by which an RNA binding protein recognizes mRNAs that do not contain an ARE is not known.

In vitro binding assays using RNA binding proteins have shown that the mRNAs that are associated with a particular RNA binding protein are often structurally or functionally related. However, these in vitro methods do not reflect the dynamic nature of mRNA association with MRNP complexes in vivo, which changes in response to intra- and inter-cellular signaling events. A need therefore exists for reliable methods for monitoring RNA binding protein-mRNA interactions, as well as the association of mRNAs and proteins with mRNP complexes in vivo. The use of such methods will allow for the characterization of mRNA-protein interactions and their functional implications, will elucidate biological pathways, and will further allow for the identification of therapeutic targets and therapeutics.

SUMMARY OF THE INVENTION

The invention provides methods and compositions that are used to identify, utilize, and characterize mRNP complexes to identify functionally related gene products that are coordinately expressed and associated with a particular mRNP complex. The gene products associated with a particular mRNP complex are classified into biologically relevant subsets on the basis of structural and/or functional relationships. These gene products, including mRNAs, RNA binding proteins, other mRNP complex-associated proteins, may participate in a particular biological pathway, such as an enzyme pathway, or may participate in other cellular event or pathology, such as tumor growth, apoptosis, differentiation, aging, or cell toxicity, for example. The functionally and structurally related gene products that are identified and quantified create a ribonomic profile for the cell or population of cells. This ribonomic profile provides a snapshot of the flow of genetic information at a given time in the life of the cell or cell population, in a normal or diseased state, or in response to an environmental influence or drug. The ribonomic profile is used as a diagnostic marker for disease or other cellular event and to rapidly identify therapeutic targets and therapeutics that alter the expression of one or more of the mRNP complex-associated gene products. The identified gene products themselves are also used as diagnostic and therapeutic indicators.

For example, the invention provides methods for diagnosing a disease or risk of disease, as well as monitoring a disease state, by identifying and monitoring changes in the expression of mRNP complex-associated gene products in a subject's cell sample and comparing the gene expression to that of a normal subject or other non-diseased cell sample. For example, the invention is useful for assessing the cell types present in a population of cells, such as in a tumor, biopsy, or body fluid, by comparing the ribonomic profile of a cell sample to signature RNP profiles characteristic of certain cell types. The identification of certain cell types is useful for diagnosing a tumor or other cellular pathology and for indicating a treatment regimen.

The invention provides useful methods for identifying a therapeutic target by contacting a cell sample with a test compound, isolating mRNP complexes, and identifying an mRNP complex component whose expression is altered in response to the compound. The therapeutic target may be any component of the RNP complex or a gene or RNA encoding the component. For example, the RNAs isolated from an RNP complex may be used to probe nucleic acid arrays to identify which genes are affected by the test compound.

The invention also provides methods for assessing the efficacy of a test compound as a therapeutic. A cell sample is contacted with a test compound and the mRNP complexes of the cell sample are used to prepare a ribonomic profile that demonstrates changes in expression of gene products associated with the mRNP complexes. A difference in the level of expression of the gene products in the treated cell sample compared to the levels in an untreated cell sample is indicative that the test compound is a candidate therapeutic.

The invention may also be used to determine the toxicity of a test compound and to identify genes that participate in cell death. Toxicity can be determined by treating a cell sample with different doses of a test compound, as described above. An array containing nucleic acids that encode regulatory molecules, such as transcription factors, is probed using the RNA isolated from a particular RNP complex, in order to identify the transcription factors, RNA binding proteins, or any other transcriptional, post-transcriptional, translational, or post-translational regulator whose expression is altered in the presence of specific toxicants, in order to identify downstream genes affected by changes in these regulators.

BRIEF DESCRIPTION OF THE DRAWINGS

FIGS. 4A and 4B show examples of mMyc and mCyc-1 multiprobe template sets, respectively. Lanes: (1) undigested riboprobe (slightly larger than RNase-digested product due to riboprobe plasmid template); (2) total cellular RNA; (3) rabbit pre-bleed serum control; (4) mRNAs extracted from HuB mRNP complexes; (5) mRNAs extracted from poly A-binding protein (PABP) mRNP complexes. An asterisk (*) denotes mRNA species not detected in total RNA.

FIG. 6 shows the results of illustrative Example 2B, below, and shows mRNAs associated with mRNP complexes using cDNA arrays. Panels: (A) pre-bleed; (B) HuB, mRNP complexes; (C) eIF-4E mRNP complexes; (D) poly A-binding protein (PABP) mRNP complexes; (E) total cellular RNA. An example of the specificity of the procedure is indicated by the differential abundance of the mRNAs encoding β-actin and ribosomal protein S29 among the mRNP profiles (arrows a and b, respectively).

DETAILED DESCRIPTION

Figure 1:
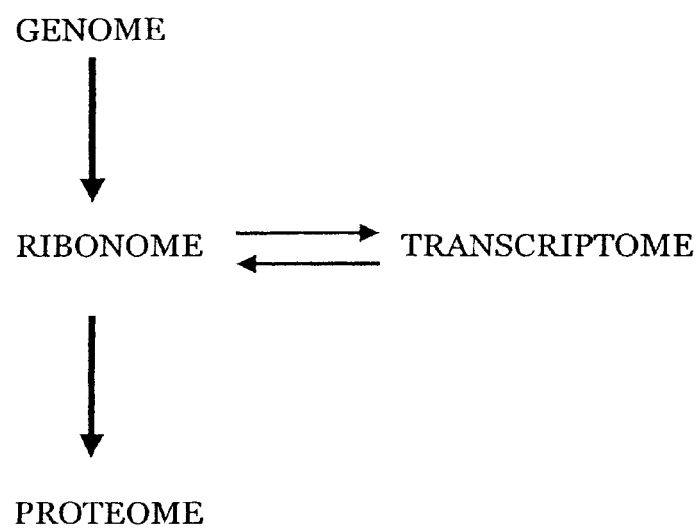
FIG. 1 is a schematic overview of the flow of genetic information from the genome to the proteome, the intermediate levels represented by the ribonome and the transcriptome. The transcriptome represents the total mRNA complement of the genome, but does not necessarily correlate directly with protein production. The processing, transport and translation of mRNA occurs in the ribonome, which represents the dynamic regulatory steps that determine the proteomic outcome.

The present invention provides methods for mining and characterizing the cellular ribononome by identifying and measuring the mRNAs and proteins that are functionally co-associated with mRNA-protein (mRNP) complexes. The invention focuses on obtaining and utilizing the genetic regulatory information residing along the protein biosynthetic pathway between the genome and the proteome (FIG. 1).

The present invention identifies the components of mRNA-protein (mRNP) complexes as a valuable tool for diagnosing, monitoring, or assessing the metabolic and disease state of cells, for identifying potential therapeutic targets, and for identifying and assessing the efficacy or toxicity of potential therapeutics. Moreover, the present invention provides methods for identifying and characterizing structurally and/or functionally related gene products, to elucidate biological pathways or processes.

Generally, an mRNP complex consists of various components that may include, but are not limited to, at least one RNA binding protein, at least one associated or bound mRNA, at least one associated or bound protein (i.e., an mRNP complex-associated protein), and may also consist of other associated or bound molecules (e.g., carbohydrates, lipids, vitamins, etc.). A component associates with an mRNP complex if it binds or otherwise attaches to the mRNP complex with a Kd of about $10^{-6}$ to about $10^{-9}$. In a preferred embodiment, the component associates with the complex with a Kd of about $10^{-7}$ to about $10^{-9}$. In a more preferred embodiment, the component associates with the complex with a Kd of about $10^{-8}$ to about $10^{-9}$.

The associated or bound mRNAs are categorized into distinct subsets based on their association with a particular RNA binding protein or mRNP complex-associated protein. By isolating each mRNP complex in a cell, and, preferably, identifying the components of the mRNP complex and the gene precursors and gene products of those components, a ribonomic gene expression profile for that cell can be generated. By identifying the mRNA components of a cellular ribonome, the cellular transcriptome can be broken down into a series of subprofiles that together can be used to define the gene expression state of a cell or tissue (see FIG. 2). Ribonomic profiles will differ from cell sample to cell sample, depending on a variety of factors including, but not limited to, the differentiation status of the cell, the species or tissue type of the cell, the developmental stage of the cell, the pathogenicity of the cell (e.g., if the cell is infected, is expressing a deleterious gene, is lacking a particular gene, is not expressing a particular gene, or is overexpressing a particular gene), the specific ligands used to isolate the mRNP complexes, the various conditions affecting the cell (e.g., environmental, apoptotic or stress states, and disease or other disorder) and other factors known to practitioners in the art.

Isolation of mRNP Complexes

An mRNP complex is isolated from a natural biological sample such as a tissue, a cell, a body fluid, an organ, or an organism. In a preferred embodiment, the biological sample is obtained from a population of cells. The population of cells may contain a single cell type. Alternatively, the population of cells may contain a mixture of different cell types from either primary or secondary cultures or from a complex tissue such as a tumor.

In one embodiment, the mRNP complex is isolated from a cell sample in which the expression of a component of an mRNP complex has been altered, e.g., induced or inhibited. In another embodiment, a particular mRNP complex or component or precursor for one or more components of the mRNP complex has been introduced into the sample or has been genetically altered. Introduction of the one or more mRNP complex components may occur by infection, transformation, or other similar methods known in the art. In one embodiment, an expression vector expressing one or more components of an mRNP complex is transfected into the cell. Suitable vectors include, but are not limited to, recombinant vectors such as plasmid vectors or viral vectors. The component is preferably operatively linked to appropriate promoter and/or enhancer sequences for expression in the cell. In an embodiment of the invention, a specific cell type is engineered to contain a cell type-specific or inducible gene promoter that drives expression of an RNA binding protein. A ligand, such as an antibody that is specific for this RNA binding protein, may immunoprecipitate the RNA binding protein, with its attached or associated mRNAs, from a tissue extract containing the cell type of interest. The RNAs are then identified to form the expression profile of that cell type or isolated for further research, as described herein.

Alternatively, the cell sample may contain a knock out cell line or knock out organism that either does not express a component of the mRNP complex or expresses decreased levels of the component. Preferably, the knock out cell line or knock out organism does not express a particular RNA binding protein, an mRNA associated with the mRNA complex or RNA binding protein, or an mRNP complex-associated protein.

In a preferred embodiment, the nucleic acid encoding the mRNP complex component is tagged (e.g., a tagged RNA binding protein) in order to facilitate the separation, observation and/or detection of the components. Accessible epitopes may be used or, where the epitopes on the components are inaccessible or obscured, epitope tags on ectopically expressed recombinant proteins may be used. Suitable tags include, but are not limited to, biotin, the MS2 protein binding site sequence, the U1snRNA 70k binding site sequence, the U1snRNA A binding site sequence, the g10 binding site sequence (Novagen, Inc., Madison, Wis.), and FLAG-TAG® (Sigma Chemical, St. Louis, Mo.). For example, a transformed cell containing a transfected vector directing the expression of a tagged RNA binding protein can be mixed with other cell types or can be implanted in an animal or human subject. In an embodiment, a ligand, such as an antibody or antibody fragment, that is specific for the tag is used to immunoprecipitate the tagged RNA binding protein with its associated mRNAs from a tissue extract containing the transformed cell. The mRNP complexes and associated RNAs can then be identified either to form an expression profile for that cell type for further analysis.

The expression of one or more mRNP complex components may be altered by contacting or treating the cell sample with a known or test compound. The compound may be, but is not limited to, a protein, a nucleic acid, a peptide, an antibody, an antibody fragment, a small molecule, or an enzyme. Where the compound is a nucleic acid, the nucleic acid may be an antisense nucleic acid, a ribozyme, an RNAi, an aptamer, a decoy nucleic acid, or a competitor nucleic acid. In one embodiment, the compound may alter the expression of an mRNP complex component through competitive binding. A compound may inhibit binding between an RNA binding protein and an mRNA, between an RNA binding protein and an mRNP complex-associated protein, or between an mRNA and an mRNP complex-associated protein, for example. In another embodiment, the cell sample is infected with a pathogen, such as a virus, bacteria, prion, fungus, parasite, or yeast, to alter expression of one or more mRNA complexes.

While any method for the isolation of an mRNP complex may be used in the present invention, the methods disclosed in co-pending U.S. application Ser. Nos. 09/750,401 and 10/238,306 are preferred, the disclosures of which are hereby incorporated by reference. The in vivo methods for isolating an mRNP complex involve contacting a biological sample that includes at least one mRNP complex with a ligand that specifically binds a component of the mRNP complex. For example, the ligand may be an antibody, a nucleic acid (e.g., an antisense, aptamer, or RNAi molecule), or any other compound or molecule that specifically binds the component of the complex. In certain embodiments, the ligand is obtained by using the serum of a subject that has a disorder known to be associated with the production of mRNP complex-specific antibodies or proteins. Examples of these disorders include autoimmune disorders and a number of cancers. In certain embodiments, the ligand is tagged with another compound or molecule in order to facilitate the separation, observation or detection of the ligand. In one embodiment of the invention, the ligand is epitope tagged, as described in the art.

In an embodiment, the mRNP complex is separated by binding the ligand (now bound to the mRNP complex) to a binding molecule that specifically binds the ligand. The binding molecule may bind the ligand directly (e.g., a binding partner specific for the ligand), or may bind the ligand indirectly (e.g., a binding partner specific for a tag on the ligand). Suitable binding molecules include, but are not limited to, protein A, protein G, and streptavidin. Binding molecules may also be obtained by using the serum of a subject suffering from a disorder such as an autoimmune disorder or cancer. In an embodiment, the ligand is an antibody that binds a component of the mRNP complex via its Fab region and a binding molecule binds the Fc region of the antibody.

In an embodiment, the binding molecule is attached to a support (e.g., a solid support such as a bead, well, pin, plate, or column). Accordingly, the mRNP complex is attached to the support via the ligand and binding molecule. The mRNP complex may then be collected by removing it from the support (e.g., by washing or eluting it from the support using suitable solvents and conditions that are known to a skilled artisan).

In certain embodiments of the invention, the mRNP complex is stabilized by cross-linking prior to binding the ligand thereto. Generally, cross-linking involves covalent binding (e.g., covalently binding the components of the mRNP complex together). Cross-linking may be carried out by physical means (e.g., by heat or ultraviolet radiation), or chemical means (e.g., by contacting the complex with formaldehyde, paraformaldehyde, or other known cross-linking agents), methods of which are known to those skilled in the art. In other embodiments, the ligand is cross-linked to the mRNP complex after binding to the mRNP complex. In additional embodiments, the binding molecule is cross-linked to the ligand after binding to the ligand. In yet another embodiment, the binding molecule is cross-linked to the support.

The methods of the invention allow for the isolation and characterization of a plurality of mRNP complexes simultaneously (e.g., "en masse"). For example, a biological sample is contacted with a plurality of ligands each specific for different mRNP complexes. A plurality of mRNP complexes from the sample bind the appropriate specific ligands. The plurality of mRNP complexes are then separated using appropriate binding molecules, thereby isolating the plurality of mRNP complexes. The mRNP complexes and the mRNAs contained within the mRNP complexes are then characterized and/or identified by methods described herein and known in the art. Alternatively, the methods of the invention are carried out on a sample numerous times and the mRNP complexes are characterized and identified in a sequential fashion, with each iteration utilizing a different ligand.

Amplification of the mRNA isolated according to the methods of the invention and/or the cDNA obtained from the mRNA is not necessary or required by the present invention. However, the skilled artisan may choose to amplify the nucleic acid that is identified according to any of the numerous nucleic acid amplification methods that are well-known in the art (e.g., polymerase chain reaction (PCR), reverse transcriptase polymerase chain reaction (RT-PCR), quantitative polymerase chain reaction (QT-PCR), or strand displacement analysis (SDA)).

Analysis of Isolated mRNP Complexes

The present invention provides methods for assessing the metabolic or gene expression state of a cell. Following isolation of at least one mRNP complex, the level of expression of at least one mRNA associated with the mRNP complex and/or at least one mRNP complex-associated protein is determined. In an embodiment, the level of expression of the mRNA(s) or the mRNP complex-associated protein(s) on a particular mRNP complex provides a subprofile that is indicative of, for example, the gene expression of a subset of functionally related gene products. In an embodiment, a subset of mRNAs associated with a particular mRNP complex identifies a ribonomic subprofile that is characteristic of a functional RNA network or biological pathway. The collection of mRNA subsets for any particular cell or tissue sample constitutes a gene expression profile, and, more specifically, a ribonomic gene expression profile, for that cell or tissue. It will be appreciated that ribonomic profiles may differ from cell to cell as described previously. Thus, the ribonomic profile of a cell can be used as an identifier for the cell and can be compared with profiles or subprofiles of other cells.

Accordingly, in one aspect, the present invention provides diagnostic methods for assessing the cell types present in a sample or a population of cells. The method involves isolating at least one mRNP complex and detecting the expression of at least one component of the mRNP complex, wherein the at least one component is specific for a certain cell type, so that the detection of the expression of the component is indicative of the presence of the cell type in the population of cells. The component may be specific for a certain cell type within an entire sample (e.g., tissue or organism) or within the population of cells. The sample or population of cells may be, for example, a tumor, a tissue, a cultured cell, a body fluid, an organ, a cell extract or a cell lysate. The methods of the invention may also be used to determine the cell types present in a population of cells, where cell type may refer to the traditional types of cells including, but not limited to, endothelial, epithelial, and smooth muscle. Alternatively, cell type, as used herein, may also refer to a class of cells derived from a particular tissue, a particular species, a particular state of differentiation, a particular disease state, or a particular cell cycle, etc.

In another aspect, the invention provides methods for identifying and characterizing functionally and/or structurally related genes and gene products. At least one mRNP complex is isolated, and mRNAs and/or mRNP complex-associated proteins are identified. The functionally related gene products may participate in similar pathways including, but not limited to, enzyme pathways, pathogenesis, tumor growth, apoptosis, differentiation, aging, or cell toxicity. Genes encoding the gene products may also be identified according to standard methods.

An isolated mRNP complex can be examined, in part to determine expression of its components, as a whole, or broken into its components. The mRNP complex can be separated from the ligand as a whole, or the mRNA can be separated from the ligand-RNA binding protein complex, followed by separation of the RNA binding protein from the ligand. Alternatively, if the mRNA is bound to the ligand, the RNA binding protein can be separated from the ligand-mRNA complex, and the mRNA then separated from the ligand. Practitioners in the art are aware of standard methods of separating the components, including washing and chemical reactions. After separation, each component of an mRNP complex can be examined and their identity, quantity, or other identifying factors preferably recorded (e.g., in a computer database) for future reference.

cDNAs can be used to identify complementary mRNAs on mRNP complexes partitioned according to methods disclosed herein. cDNA microarray grids can be used to identify mRNA subsets en masse. Microarrays are precisely aligned grids in which each target nucleic acid (e.g., cDNA, oligonucleotide, or gene) has a position in a matrix of carefully spotted cDNAs. Each target nucleic acid examined on a microarray has a precise address that can be located, and the binding can be quantitated. Microarrays may be arranged in a commercially available substrate (e.g., paper, nitrocellulose, nylon, any other type of membrane filter, chip, such as a siliconized chip, glass slide, silicone wafer, or any other suitable solid or flexible support). In addition, mRNAs in a sample can be identified based upon the stringency of binding and washing, a process known as "sequencing by hybridization."

Alternative approaches for identifying, sequencing and/or otherwise characterizing the mRNAs in an mRNA subset include, but are not limited to, differential display, phage display/analysis, SAGE (Serial Analysis of Gene Expression), and preparation of cDNA libraries from the mRNA preparation and sequencing of the members of the library.

Methods for DNA sequencing that are well known and generally available in the art may be used to practice any of the embodiments of the invention. The sequencing methods may employ such enzymes as the Klenow fragment of DNA polymerase I, SEQUENASE® (U.S. Biochemical Corp, Cleveland, Ohio), Taq polymerase (Perkin Elmer, Boston, Mass.), thermostable T7 polymerase (Amersham, Chicago, Ill.), or combinations of polymerases and proofreading exonucleases such as those found in the Elongase® Amplification System marketed by Gibco BRL (Invitrogen™, Carlsbad, Calif.). Preferably, the process is automated with machines such as the Hamilton Micro Lab 2200 (Hamilton, Reno, Nev.), Peltier Thermal Cycler (PTC200) (MJ Research, Watertown, Mass.) and the ABI Catalyst and 373 and 377 DNA Sequencers (Perkin Elmer, Shelton, Conn.).

Figure 2A:
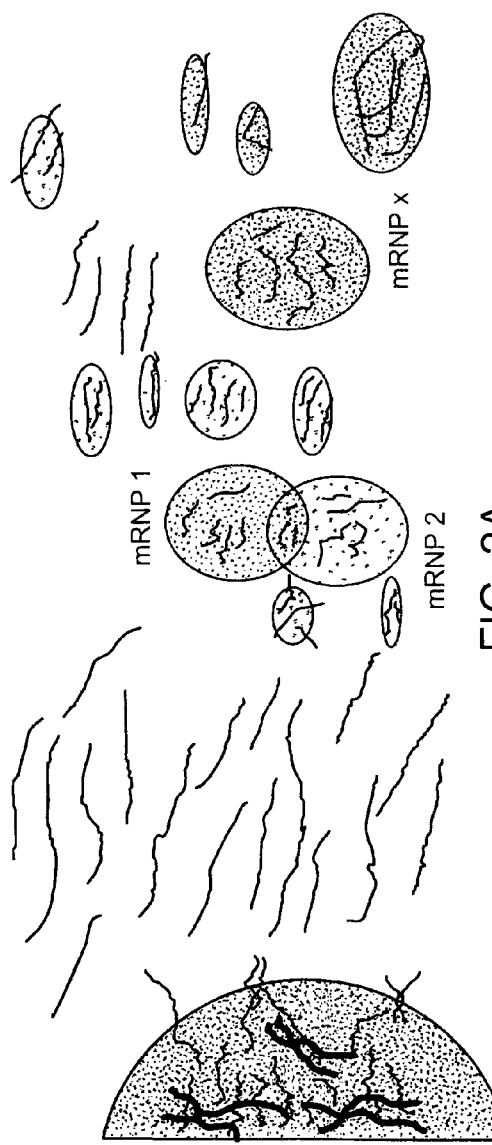
FIG. 2A is an illustration showing transcription of mRNAs that associate with mRNP complexes (e.g., mRNP1, mRNP2, mRNPX).
Figure 2B:
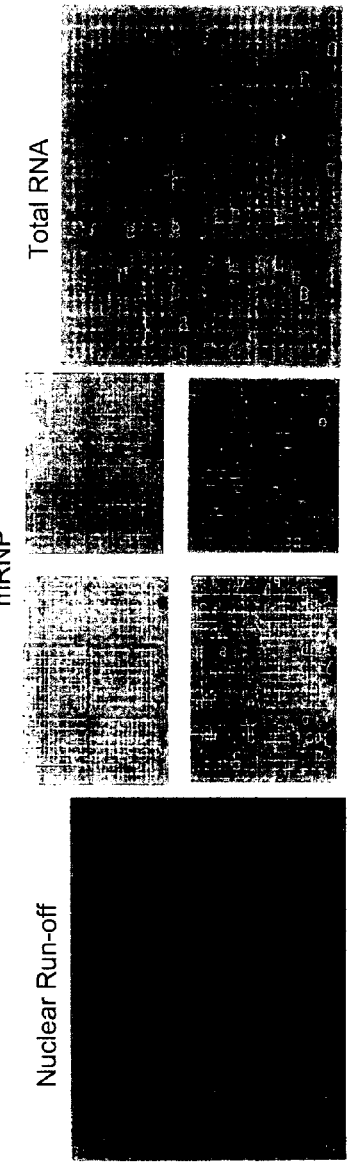
FIG. 2B is an illustration comparing arrays of total cellular mRNA, nuclear run-off mRNA, and mRNA that is bound within mRNP complexes.

In an embodiment, the methods of the invention are carried on isolated nuclei from cells (e.g., that are undergoing developmental or cell cycle changes or that have otherwise been subjected to a cellular or an environmental change), performing nuclear run-off assays according to known techniques to obtain transcribing mRNAs, and then comparing the transcribing mRNAs with the global mRNA levels isolated from mRNP complexes from the same cells using cDNA microarrays. These methods thus provide methods for distinguishing transcriptional from post-transcriptional effects on steady state mRNA levels en masse. For example, FIG. 2 is a graphical illustration comparing the total cellular mRNA (the transcriptome), nuclear run-off mRNA, and mRNA that is bound within mRNP complexes to form a part of the ribonome. The total RNA inset depicts the total mRNA expressed in the cell (transcriptome) as a microarray. A microarray representing a nuclear run-off experiment (lower far left) can be derived by transcription using isolated nuclei and analysis on Atlas™ arrays (BD Biosciences Clontech, Palo Alto, Calif.). As opposed to a total RNA or transcription profile that depicts RNA accumulation representing a steady-state level of mRNA, which is affected by transcriptional and post-transcriptional events, the mRNAs detected by nuclear run-off experiments represent only the transcription of a gene before the influence of post-transcriptional events. The microarrays representing mRNP complexes contain discrete and more limited subsets of mRNAs than the transcriptome or nuclear run-offs. The mRNP complex microarrays are labeled mRNP-1 through mRNP-X and depict multiple mRNAs found in mRNP complexes isolated by using antibodies reactive with mRNA-associated proteins.

Other methods for characterizing and identifying mRNP complex components include standard laboratory techniques such as, but not limited to, reverse transcription or quantitative PCR, RNAse protection, Northern Blot analysis, Western blot analysis, macro- or micro-array analysis, in situ hybridization, immunofluorescence, radioimmunoassay, and immunoprecipitation. The results obtained from these methods are compared and contrasted in order to further characterize the functional relationships of the mRNA subsets and other mRNP components.

RNA binding proteins and mRNP complex-associated proteins useful in the practice of the present invention are known in the art, or may alternatively be identified and discovered by the methods described herein. RNA binding proteins are involved in the control of a variety of cellular regulatory and developmental processes, such as RNA processing and compartmentalization, mRNA splicing and transport, RNA stabilization, mRNA translation, and viral gene expression. Examples of useful RNA binding proteins include poly A-binding protein ("PABP"), and the four ELAV/Hu mammalian homologues of the Drosophila ELAV RNA binding protein. HuA (HuR) is ubiquitously expressed while HuB, HuC and HuD (and their respective alternatively-spliced isoforms) are predominantly found in neuronal tissue. HuB, HuC and HuD are also expressed as tumor cell-specific antigens in some small cell carcinomas, neuroblastomas, and medulloblastomas. All Hu proteins contain three RNA-recognition motifs, which confer their binding specificity for AU Rich Instability Elements (AREs). Hu proteins bind in vitro to several ARE-containing early response gene mRNAs including c-myc, c-fos, GM-CSF and GAP-43. The binding of Hu proteins to ARE-containing mRNAs can result in the stabilization and increased translatability of the mRNA transcripts. The neuron-specific Hu proteins are one of the earliest neuronal markers produced in teratocarcinoma cells following retinoic acid treatment to induce neuronal differentiation.

Other exemplary RNA binding proteins are selected from the RNA Recognition Motif family of cellular proteins involved in pre-mRNA processing. One example of such a protein is the U1A snRNP protein. More than 200 members of the RNA Recognition Motif superfamily have been reported to date, the majority of which are ubiquitously expressed and conserved in phylogeny. Most have binding specificity for polyadenylate mRNA or small nuclear ribonucleic acids (e.g., U1, U2, etc.), transfer RNAs, 5S or 7S RNAs. They include, but are not limited to, hnRNP proteins (A, B, C, D, E, F, G, H, I, K, L), RNA Recognition Motif proteins CArG, DT-7, PTB, K1, K2, K3, HuD, HUC, rbp9, eIF4B, sxl, tra-2, AUBF, AUF, 32 KD protein, ASF/SF2, U2AF, SC35, and other hnRNP proteins. Tissue-specific members of the RNA Recognition Motif family are less common, including IMP, Bruno, AZP-RRM1, X16 which is expressed in pre-B cells, Bj6 which is a puff-specific Drosophila protein and ELAV/Hu, which is neuron specific. RNA binding proteins and mRNP complex-associated proteins useful in the practice of the present invention include those isolated using autoimmune and cancer patient sera. A non-comprehensive list of RNA binding proteins and mRNP complex-associated proteins useful in the practice of the present invention is set forth below in Table 1.

TABLE 1

RNA Binding and mRNP Complex-Associated Proteins

| | | |
|---|---|---|
| SLBP | DAN | TTP |
| Hel-N1 | Hel-N2 | eIF-4A |
| eIF-4B | eIF-4G | eIF-4E |
| eIF-5 | eIF-4EBP | MNK1 |
| PABP | p62 | KOC |
| p90 | La | Sm |
| Ro | U1-70K | AUF-1 |
| RNAse-L | GAPDH | GRSF |
| Ribosomal P0, P1, P2/L32 | PM-Scl | FMR |
| Stauffen | Crab 95 | TIA-1 |
| Upf1 | RNA BP1 | RNA BP2 |
| RNA BP3 | CstF-50 | NOVA-1 |
| NOVA-2 | CPEBP | GRBP |
| SXL | SC35 | U2AF I |
| ASF/SF2 | ETR-1 | IMP-1 |
| IMP-2 | IMP-3 | ZBP |
| LRBP-1 | Barb | PTB |
| UPAmRNA BP | BARB1 | BARB2 |
| GIFASBP | CYP mRNA BP | IRE-BP |
| p50 | RHA | FN mRNA BP |
| AUF-1 | GA mRNA BP | Vigillin |
| ERBP | CRD-BP | HuA |
| HuB | HuC | HuD |
| HnRNP A | hnRNP B | hnRNP C |
| HnRNP D | hnRNP B | hnRNP F |
| HnRNP G | hnRNP H | hnRNP K |
| HnRNP L | U2AF | |

Figure 3:
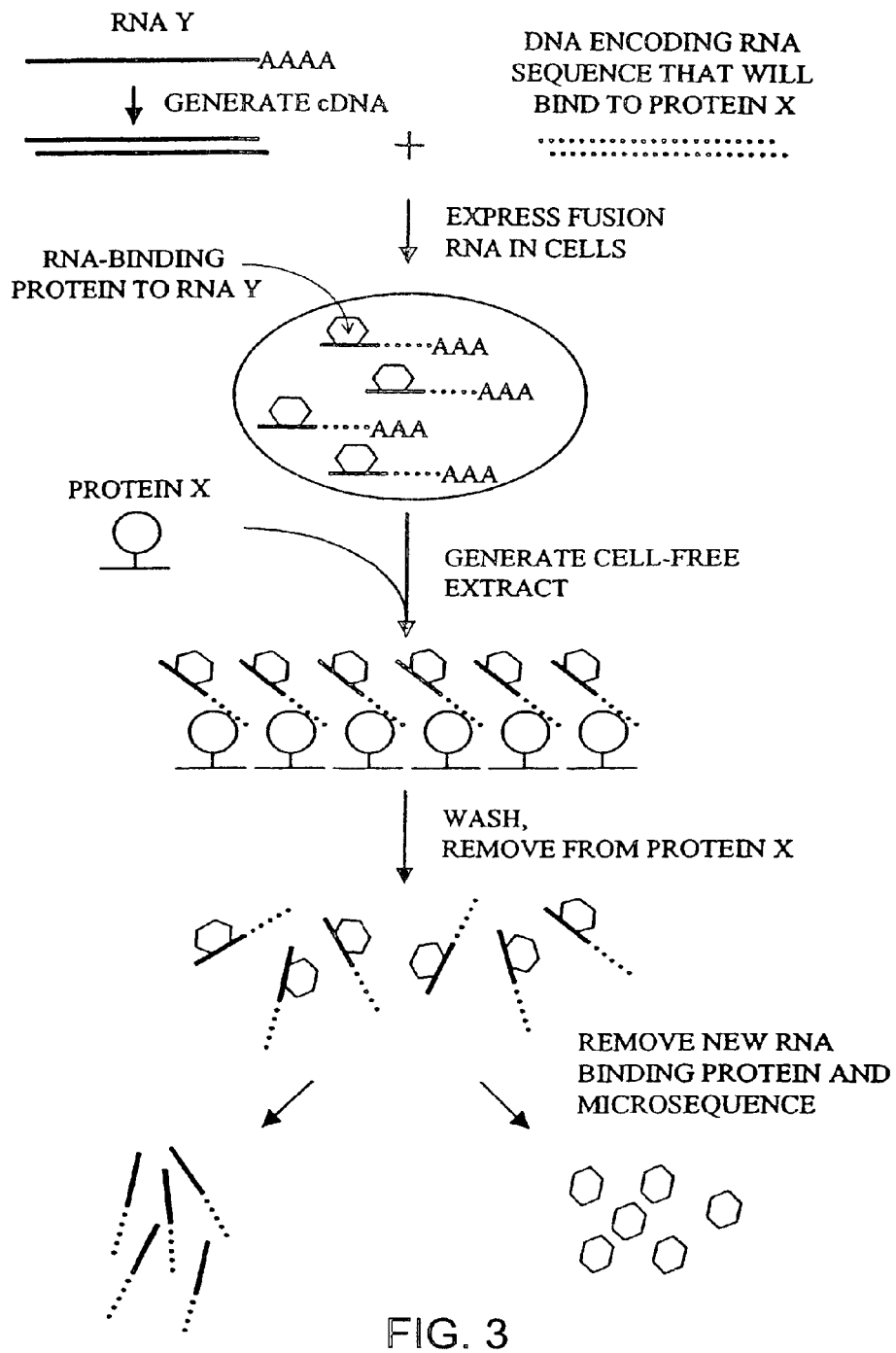
FIG. 3 is a schematic outlining a strategy for the identification of new RNA binding proteins.

The techniques described herein are used to identify new (i.e., novel or previously unknown) RNA binding proteins and mRNP complex-associated proteins (FIG. 3). Thus, in one embodiment of the invention, an mRNA of interest (depicted in FIG. 3 as "RNA Y") is used as "bait" to trap a new RNA binding protein. Preferably, RNA Y is first converted to a cDNA using standard molecular biology techniques and is subsequently ligated at the 3' or 5' end to a DNA tag that encodes a sequence that will bind a ligand of the present invention (the ligand being illustrated as protein "X" in FIG. 3). In other words, the tagged DNA encodes a binding partner of the ligand. The resulting fusion RNA is expressed in cells, where endogenous RBPs can bind and interact with RNA Y.

The cells are then lysed and cell-free extracts are prepared and contacted with Protein X, which has been immobilized on a solid support matrix. After incubation, Protein X and the attached RNA fusion molecule and its associated RNA binding proteins are washed to remove residual cellular material. After washing, the newly isolated RNA binding proteins are removed from the RNA-protein complex and identified by protein microsequencing. Useful ligands include mRNP complex-specific antibodies or proteins (e.g., obtained from a subject with an autoimmune disorder or cancer) or proteins (e.g., MSII coat protein). Useful binding partners include antibodies specific for the ligand.

Once partial protein sequence is obtained, the corresponding RNA binding protein gene may be identified from known databases of cDNA and genomic sequences or isolated from a cDNA or genomic library and sequenced. Preferably, the gene is isolated, the protein is expressed, and an antibody is generated against the recombinant RNA binding protein using known techniques. The antibodies are then used to recover and confirm the identity of the endogenous RNA binding protein. Subsequently, the antibody can be used for ribonomic analysis to determine the subset of cellular RNAs that cluster with (i.e., associate with) RNA Y. The RNA binding protein is further tested for its ability to regulate the translation of the protein encoded by RNA Y, and is tested for validation as a drug target. Likewise, proteins encoded by the cellular RNAs that cluster with RNA Y are tested for validation as drug targets, as further described herein.

Identification of Therapeutic Targets

The invention provides methods for identifying a therapeutic target by comparing the ribonomic subprofiles of a cell sample to the ribonomic subprofiles of a control sample. A difference in the expression of a component of an mRNP complex between the two samples is indicative that the component is a candidate therapeutic target. The therapeutic target may include, but is not limited to, any component of an mRNP complex, or nucleic acid or gene product thereof. In an embodiment of the invention, the cell sample is treated with a test compound and the control sample comprises cells that have not been treated with the test compound. In another embodiment, the control sample comprises cells at a different stage in their growth cycle from the cells in the cell sample. In yet another embodiment, the cell sample comprises a tumor cell or other diseased cell, and the control sample comprises a normal cell. Target identification includes methods known to practitioners in the art, such as, but not limited to, the use of screening libraries, peptide phage display, cDNA microchip array screening, and combinatorial chemistry techniques known to practitioners in the art. A summary of the steps for target discovery is provided in FIG. 9.

Identification of Therapeutics

In another aspect, the invention provides methods for assessing the efficacy of a test compound as a therapeutic. A cell sample is contacted with a test compound and a ribonomic profile or subprofile of the cell sample comprising the expression of at least one gene product associated with at least one mRNP complex is prepared. The expression levels of the gene product in the cell sample are compared to the expression levels of the gene product in a control sample (e.g., a cell sample that is not contacted with a test compound). Identification of a difference in expression of the gene product between the treated and untreated cell samples is indicative that the test compound is a potential therapeutic. Test compounds may be, for example, nucleic acids, hormones, antibodies, antibody fragments, antigens, cytokines, growth factors, pharmacological agents (e.g., chemotherapeutics, carcinogenics, or other cells), chemical compositions, proteins, peptides, and/or small molecules.

In various embodiments of the invention, the therapeutic may stabilize or destabilize the mRNA or the mRNP complex-associated protein. In another embodiment, the therapeutic may either inhibit translation of the mRNA, inhibit transport of the mRNA or the mRNP complex-associated protein, inhibit the binding of the RNA binding protein to the mRNA, inhibit the binding of the RNA binding protein to the mRNP complex-associated protein, or inhibit the binding of the mRNA to the mRNP complex-associated protein, for example.

In another aspect, the invention provides methods for assessing toxicity, potential side effects, specificity or selectivity of a test compound, for example, by altering the concentrations or amounts of a test compound used to treat a cell sample.

In yet another aspect, the present invention provides methods for assessing or monitoring the efficacy of a therapeutic in a subject. In accordance with the invention, an effective amount of a therapeutic is administered to a subject. At least one mRNP complex is isolated from a cell sample from the subject, wherein altered expression of a gene product associated with the mRNP complex is altered by administration of the therapeutic. The expression of the gene product in the cell sample after administration of the therapeutic is compared to the expression of the gene product in a control sample (e.g., a second cell sample obtained either prior to administration of the therapeutic or from a normal subject). A difference in expression between the treated and the control cell samples is indicative of the efficacy of the therapeutic. The above tests can be repeated over a period of time to monitor the continued efficacy of the therapeutic.

Therapeutics may target over- or under-expressed proteins involved in the etiology of a disease, disorder, or condition. Such over- or under-expression may result in destabilization or stabilization of RNA.

Therapeutics that Destabilize mRNA

If a disease, condition or disorder is characterized by overexpression of a protein, a therapeutic for treatment of such a condition will reduce or eliminate expression of the protein. For example, since RNA binding proteins enhance the stability of short-lived mRNAs encoding protooncogenes, growth factors and cytokines that contribute to cell proliferation, inhibition of RNA binding protein production may alleviate diseases such as cancers or autoimmune diseases (e.g., by decreasing tumor growth or inflammation, respectively). In addition, RNA binding protein overexpression in several human tumors correlates with resistance to chemotherapy and UV irradiation. Increased stability of c-fos, c-myc, cyclin B1 and other short-lived mRNAs in response to UV-irradiation or therapeutic drugs is well known. Accordingly, inhibition of RNA binding protein expression in these tumors destabilizes the mRNA in the tumors and, as a result, renders the tumors more responsive to cancer treatments.

In order to reduce overexpression or to cease expression of a protein of interest, the mRNA can be destabilized by administering an effective amount of a suitable test compound (e.g., an RNA binding protein inhibitor) either in vitro or in vivo. The test compound may bind mRNA so as to inhibit RNA binding protein binding to the mRNA, bind the RNA binding protein so as to inhibit RNA binding protein binding to the mRNA, bind to and destabilize the mRNP complex, and/or bind the mRNA so as to directly destabilize the mRNA, for example. Compounds that bind to the mRNA but that do not stabilize the mRNA may inhibit the ability of an RNA binding protein to stabilize the mRNA. If the compound binds competitively with an RNA binding protein, the compound can decrease mRNA stability by inhibiting the RNA binding protein's ability to bind the mRNA.

Alternatively, the test compound may inhibit RNA binding protein or mRNA expression.

Effective test compounds (e.g., RNA binding protein inhibitors) can be readily determined by screening compounds for their ability to interfere with the production of RNA binding protein or their ability to inhibit the binding to, and/or stabilization of, mRNA, for example, by methods described herein. Compounds that function by inhibiting RNA binding protein or mRNA production can be identified by exposing cells that express the RNA binding protein or mRNA of interest and monitoring the levels of RNA binding protein or mRNA, respectively. Compounds that function by inhibiting the stabilizing effect of RNA binding protein on mRNA can be identified by combining RNA binding protein and an mRNA that would otherwise be stabilized, adding compounds to be evaluated as RNA binding protein inhibitors, and monitoring the binding affinity of RNA binding protein and the mRNA. Compounds that increase or decrease the binding affinity of RNA binding protein and the mRNA can be readily determined by art known methods.

Therapeutics that Stabilize mRNA

If a disease, condition or disorder is characterized by underexpression of an mRNA stabilizing protein, a therapeutic for treatment of such a medical condition may operate by stabilizing the mRNA associated with the underexpressed protein. Accordingly, mRNA may be stabilized by administering an effective amount of a compound, either in vitro or in vivo. The compound may possess a similar binding ability and stabilizing effect as the RNA binding protein or, may promote the RNA binding protein's ability to stabilize mRNA, and/or may promote the production of the stabilizing RNA binding protein or the mRNA of interest. Such a compound may be referred to as an RNA binding protein inducer and may operate by interacting with the mRNA, the RNA binding protein or both. Alternatively, mRNA can be stabilized by administering an effective amount of a suitable RNA binding protein that possesses the necessary mRNA stabilizing effect.

Compounds that increase RNA binding protein production can be identified by initially exposing cells that express the RNA binding protein to potential inducers and, monitoring the levels of the RNA binding protein, in accordance with the methods described above. If the level of RNA binding protein expression increases, the compound is an RNA binding protein inducer. Compounds that inhibit RNA binding protein binding to mRNA, but which bind and stabilize mRNA, can be identified by methods disclosed herein. A skilled practitioner may combine RNA binding protein and an mRNA that would otherwise be stabilized, add a compound, and monitor the binding affinity of the RNA binding protein and the mRNA. Compounds that increase or decrease the binding affinity of an RNA binding protein and the mRNA can be readily determined by evaluating the binding affinity of the RNA binding protein to the mRNA after exposure to the compound, as described herein. By monitoring the concentration of mRNA over time, those compounds which bind to the mRNA can then be assayed for their ability to stabilize mRNA.

Antibody Preparation

Antibodies and fragments thereof that bind to mRNP complexes are generated using methods that are well known in the art. Such antibodies may include, but are not limited to, polyclonal, monoclonal, chimeric, single chain, Fab fragments, and fragments produced by a Fab expression library. Antibodies and fragments thereof may also be generated using antibody phage expression display techniques, which are known in the art.

For the production of antibodies, various hosts including, but not limited to, goats, rabbits, rats, mice, and humans are immunized by injection with the mRNP complex or any fragment or component thereof that has immunogenic properties. Depending on the host species, an adjuvant is used to increase the immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (Bacilli Calmette-Guerin) and *Corynebacterium parvum* are preferable.

Monoclonal antibodies to the components of the mRNP complex are prepared using any technique that provides for the production of antibody molecules by a cultured cell line. These include, but are not limited to, the hybridoma technique, the human B-cell hybridoma technique, and the EBV-hybridoma technique. Generally, an animal is immunized with the mRNP complex or immunogenic fragment(s) or conjugate(s) thereof. Lymphoid cells (e.g., splenic lymphocytes) are then obtained from the immunized animal and fused with immortalized cells (e.g., myeloma or heteromyeloma) to produce hybrid cells. The hybrid cells are screened to identify those which produce the desired antibody.

Antibodies may also be produced by inducing in vivo production in the lymphocyte population or by screening immunoglobulin libraries or panels of highly specific binding reagents as is known in the art.

Antibody fragments that contain specific binding sites for mRNP complexes may also be generated. For example, such fragments include, but are not limited to, the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries are constructed to allow rapid and easy identification of monoclonal Fab fragments with the desired specificity.

Various immunoassays are used to identify antibodies having the desired specificity for the mRNP complex. Numerous protocols for competitive binding or immunoradiometric assays using either polyclonal or monoclonal antibodies with established specificities are well known in the art. Such immunoassays typically involve the measurement of complex formation between the component of the mRNP complex and its specific antibody. An immunoassay utilizing monoclonal antibodies reactive to two non-interfering epitopes is preferred, but a competitive binding assay may also be employed.

The invention provides kits containing columns in which antibodies to various mRNP complexes or components thereof (e.g., antibodies to RNA binding proteins) are immobilized. The antibodies may be conjugated to a support suitable for a diagnostic assay (e.g., a solid support such as beads, plates, slides or wells formed from materials such as latex or polystyrene) in accordance with known techniques. Antibodies may likewise be conjugated to detectable groups such as radiolabels (e.g., $^{35}$S, $^{125}$I, $^{131}$I), enzyme labels (e.g., horseradish peroxidase, alkaline phosphatase), and fluorescent labels (e.g., fluorescein) in accordance with known techniques. Such devices preferably include at least one reagent specific for detecting the binding between an antibody and the RNA binding protein. The reagents may also include ancillary agents such as buffering agents and protein stabilizing agents (e.g., polysaccharides and the like). The device may further include, where necessary, agents for reducing background interference in a test, control reagents, apparatus for conducting a test, and the like. The device may be packaged in any suitable manner, typically with all elements in a single container along with a sheet of printed instructions for carrying out the test.

Antibodies raised against an mRNP complex can be conjugated to a drug. Upon administration to a patient, the antibody will bind to the mRNP complex so as to deliver a relatively high concentration of the drug to the desired tissue or organ. In one embodiment, an antibody is conjugated to an anti-cancer drug, including, but not limited to, an antifolate, an anti-tumor antibiotics and other tumor-treating compounds.

Antibodies that bind to the mRNP complex can also be covalently or ionically coupled to various markers, and used to detect the presence of tumors. By administering a suitable amount of the marker-coupled antibody to a patient, allowing the antibody to bind the mRNP complex at or around a tumor site, and detecting the marker, the presence of tumors can be detected. Suitable markers are well known in the art, and include, but are not limited to, radioisotopic labels, fluorescent labels and the like. Suitable detection methods for these markers are also well known in the art and include, but are not limited to, positron emission tomography, autoradiography, flow cytometry, radioreceptor binding assays, and immunohistochemistry.

High Throughput Screening Methods for Libraries of Compounds

In an embodiment of the invention, high throughput screening assays and competitive binding assays are used to identify compounds that bind to an mRNP complex or component thereof from combinatorial libraries of compounds (e.g., phage display peptide libraries, small molecule libraries and oligonucleotide libraries).

In one embodiment, an mRNP component, catalytic or immunogenic fragment thereof, or oligopeptide thereof, can be used to screen libraries of compounds in any of a variety of drug screening techniques. An exemplary technique is described in published PCT application WO84/03584, hereby incorporated by reference. The fragment employed in such screening can be free in solution, affixed to a support (e.g., solid support), borne on a cell surface, or located intracellularly.

The SELEX method, described in U.S. Pat. No. 5,270,163 (Gold et al.), hereby incorporated by reference, is used to screen oligonucleotide libraries for compounds that have suitable binding properties. In accordance with the SELEX method, a candidate mixture of single stranded nucleic acids with regions of randomized sequence can be contacted with the mRNP complex. Those nucleic acids having an increased affinity to the mRNP complex can be partitioned and amplified so as to yield a ligand enriched mixture.

Phage display technology is used to screen peptide phage display libraries to identify peptides that bind to an mRNP complex or component thereof. Methods for preparing libraries containing diverse populations of various types of molecules such as peptides, polypeptides, proteins, and fragments thereof are known in the art and are commercially available.

A library of phage displaying potential binding peptides is incubated with an mRNP complex to select clones encoding recombinant peptides that specifically bind the mRNP complex or components thereof. After at least one round of biopanning (binding to the mRNP complex), the phage DNA is amplified and sequenced, thereby providing the sequence for the displayed binding peptides. Briefly, the target, an mRNP complex, can be coated overnight onto tissue culture plates and incubated in a humidified container. In a first round of panning, approximately $2\times10^{11}$ phage can be incubated on the protein-coated plate for 60 minutes at room temperature while rocking gently. The plates are then washed using standard wash solutions. The binding phage can then be collected and amplified following elution using the target protein. Secondary and tertiary pannings can be performed as necessary. Following the last screening, individual colonies of phage-infected bacteria can be picked at random, the phage DNA isolated and subjected to automated dideoxy sequencing. The sequence of the displayed peptides can be deduced from the DNA sequence.

The biological activity of compounds can be evaluated using in vitro assays known to those skilled in the art (e.g., protein synthesis assays or tumor cell proliferation assays). Alternatively, the biological activity of the compounds are evaluated in vivo. Various compounds, including antibodies, can bind to mRNP complexes and components thereof with varying effects on mRNA stability. The activity of the compounds once bound can be readily determined using the assays described herein.

Binding assays include cell-free assays in which an RNA binding protein and an mRNA are incubated with a labeled test compound. Following incubation, the mRNA, free or bound to a test compound, can be separated from unbound test compound using any of a variety of techniques known in the art. The amount of test compound bound to an mRNP complex or component thereof is then determined, using detection techniques known in the art.

Alternatively, the binding assay is a cell-free competition binding assay. In such assays, mRNA is incubated with labeled RNA binding protein. A test compound is added to the reaction and assayed for its ability to compete with the RNA binding protein for binding to the mRNA. Free labeled RNA binding protein can be separated from bound RNA binding protein. By subsequently determining the amount of bound RNA binding protein, the ability of the test compound to compete for mRNA binding can be assessed. This assay can be formatted to facilitate screening of large numbers of test compounds by linking the RNA binding protein or the mRNA to a support so that it can be readily washed free of unbound reactants. A plastic support (e.g., a plastic plate such as a 96 well dish) is preferred. The RNA binding protein and mRNA suitable for use in the cell-free assays described herein can be isolated from natural sources (e.g., membrane preparations) or prepared recombinantly or chemically. The RNA binding protein can be prepared as a fusion protein using, for example, known recombinant techniques. Preferred fusion proteins include, but are not limited to, a glutathione-S-transferase (GST) moiety, a green fluorescent protein (GFP) moiety that is useful for cellular localization studies or a His tag that is useful for affinity purification.

A competitive binding assay may also be cell-based. Accordingly, a compound, preferably labeled, known to bind an mRNP complex or component thereof, is incubated with the mRNP complex or component thereof in the presence and absence of a test compound. By comparing the amount of known test compound associated with cells incubated in the presence of the test compound with that of cells incubated in the absence of the test compound, the affinity of the test compound for the RNA binding protein, mRNA, and/or complex thereof can be determined. Cell proliferation can be monitored by measuring the uptake into cellular nucleic acids of labeled bases (e.g., radioactively, such as $^3$H, SiC, or $^{14}$C; fluorescently, such as CYQUANT (Molecular Probes); or calorimetrically such as rdU (Boehringer Mannheim) or MTS (Promega)) as known in the art. Cytosolic/cytoplasmic pH determinations can be made with a digital imaging microscope using substrates such as bis(carboxyethyl)-carbonyl fluorescein (BCECF) (Molecular Probes, Inc., Eugene, Oreg.).

Other types of assays that can be carried out to determine the effect of a test compound on RNA binding protein binding to mRNA include, but are not limited to, the Lewis Lung Carcinoma assay and extracellular migration assays such as the Boyden Chamber assay.

Accordingly, the methods permit the screening of compounds for their ability to modulate the effect of an RNA binding protein on the binding of and stability of mRNA. Using the assays described herein, compounds capable of binding to mRNA and modulating the effects on those cellular bioactivities resulting from mRNA stability and correlated protein synthesis are identified. The compounds identified in accordance with the above assays are formulated as therapeutic compositions.

Diagnosing and Monitoring Disease

In another aspect, the invention provides methods for diagnosing a disease or risk of a disease in a subject. A ribonomic profile from a subject's cell sample is prepared and at least one mRNP complex is analyzed. The expression of at least one gene product, for which altered expression is indicative of a disease or risk of disease, is determined. The gene product may be an RNA binding protein, an mRNA, an mRNP complex-associated protein or other gene product bound to or associated with the mRNP complex. The expression of the gene product in the cell sample is compared to the expression of the gene product in a control sample. The control sample may be either a sample of normal cells or a second cell sample from the subject. Alternatively, the control sample is a positive control from a diseased and/or normal individual. By observing the relative expression of the gene product in the cell sample compared to the control sample, the presence of a disease or risk of disease can be determined.

In another aspect, the invention discloses a method for monitoring a disease state in a subject. At least one mRNP complex is isolated from a diseased subject's cell sample, wherein the mRNP complex has at least one gene product that is associated with the disease. The expression of the gene product in the subject's cell sample is compared to the expression of the gene product in a control sample. The identification of a difference in the expression of the gene product in the diseased subject cell sample compared to the expression of the gene product in the control sample is indicative of a change in the disease state of the subject. For example, a decrease in the production of a tumor related antigen or its mRNA is indicative of decreased tumor load or remission; by contrast, an increase in expression of the tumor antigen is indicative of aggressive tumor growth. Such monitoring during drug treatment provides information about the effectiveness of the subject's drug regimen, and may indicate when a particular regimen is not, or is no longer, effective for treating the disease or condition. The control sample may be a second cell sample from the subject, preferably, obtained when the subject is free of one or more symptoms of the disease. Alternatively, the control sample is from a normal subject or other normal cell sample.

In summary, the present invention provides powerful in vivo methods for determining the ribonomic profile of a cell and detecting changes in the ribonomic profile. The invention has numerous uses, including, but not limited to, monitoring cell development or growth, monitoring a cell state, and monitoring perturbations of a biological system such as disease, condition or disorder. The invention further provides methods for diagnosing a disease, condition, or disorder and determining appropriate treatment regimens. The invention also is useful for distinguishing ribonomic profiles among organisms such as plant, fungal, bacterial, viral, protozoan, or animal species.

The present invention can be used to discriminate between transcriptional and post-transcriptional contributions to gene expression and to track the movement of RNAs through mRNP complexes, including the interactions of combinations of proteins with RNAs in mRNP complexes. Accordingly, the present invention can be used to study the regulation of RNA stability. The present invention can be used to investigate the activation of translation of mRNAs as single or multiple species by tracking the recruitment of mRNAs to active polysomes, measuring the sequential, ordered expression of mRNAs such as mRNAs that encode transcription factors or RNA binding proteins, and measuring the simultaneous, coordinate expression of multiple mRNAs. The present invention can also be used to determine the transacting functions of RNAs themselves upon contacting other cellular components. These and numerous other uses will be made apparent to the skilled artisan upon study of the present specification and claims.

The contents of all cited references (including literature references, issued patents, and patent applications) as cited through out this application are hereby expressly incorporated by reference. The following Examples are set forth to illustrate the present invention, and are not to be construed as limiting thereof.

EXEMPLIFICATION

Example 1

RNase Protection in a Multiprobe System

A multiprobe RNase protection assay was used to rapidly optimize the immuno-precipitation of several endogenous mRNP complexes containing different RNA binding proteins. In the multiprobe system, many mRNAs associated with an mRNP complex can be assayed in a single lane of a polyacrylamide gel.

Cell Culture and Transformation. Murine P19 embryonal carcinoma cells were obtained from the American Type Culture Collection (ATCC, Manassas, Va.) and maintained in monolayer culture using a-Minimum Essential Medium Eagle (MEM) without phenol red (Gibco BRL 41061-0291) (Invitrogen, Carlsbad, Calif.) supplemented with 7.5% Bovine Calf Serum (BCS), 2.5% Fetal Bovine Serum (FBS) (Hyclone, Logan, Vt.) and 100U of Penicillin/Streptomycin. Cells were grown in tissue culture flasks or plates that had been pre-coated with 0.1% gelatin (Sigma Chemicals, St. Louis, Mo.) and removed prior to use. Monolayer cell cultures were maintained in 5% $CO_2$ at 37° C.

P19 cells were stably transfected with a SV40 promoter-driven pAlpha2-gene 10-HuB plasmid that ectopically expressed a gene 10-tagged neuron-specific HuB protein termed Hel-N2. The expression of the transfected plasmid was maintained by supplementing the medium with 0.2 mg/ml G418 (Sigma Chemicals, St. Louis, Mo.). Although the construct lacks thirteen amino acids from the hinge region connecting the RNA recognition motifs 2 and 3 of Hel-N 1, the RNA recognition motifs are otherwise identical and in vitro binding experiments have indicated no differences in the AU-rich RNA binding properties of Hel-N1 and Hel-N2.

Antibodies. Monoclonal anti-gene 10 (g10) antibodies were produced according to standard techniques as previously described. Polyclonal sera reactive with HuA were produced according to standard techniques as previously described. Antibodies reactive with Poly A-binding protein (PABP) were obtained from McGill University (Canada).

Preparation of Cell Free Extracts. Cells were removed from tissue culture plates with a rubber scraper and washed with cold phosphate buffered saline (PBS). The cells were resuspended in approximately two pellet volumes of polysome lysis buffer (PLB) containing 100 mM KCl, 5 mM $MgCl_2$, 10 mM HEPES pH 7.0, and 0.5% NP-40 with 1 mM Dithiothrietol (DTT), 100 U/mL RNase OUT (Gibco BRL, Invitrogen Corp., Carlsbad, Calif.), 0.2% vanadyl ribonucleoside complex (VRC) (Gibco BRL, Invitrogen Corp., Carlsbad, Calif.), 0.2 mM Phenylmethylsulfonylfluoride (PMSF), 1 mg/mL pepstatin A, 5 mg/mL pepstatin, and 20 mg/mL leupeptin added fresh at the time of use. The cell lysate was frozen and stored at −100° C. At the time of use, the cell lysate was thawed and centrifuged at 12,000 rpm in a tabletop microfuge for 10 min at 4° C. The supernatant was removed and centrifuged a second time at 16,000 rpm in a tabletop microfuge for 5 min at 4° C. before being stored on ice or refrozen at −100° C. The mRNP containing cell lysate contained approximately 30-50 mg/mL total protein.

Immunoprecipitation. Protein A sepharose beads (Sigma Biochemicals, St. Louis, Mo.) were swollen 1:5 v/v in NT2 buffer (50 mM Tris pH 7.4, 150 mM NaCl, 1 mM $MgCl_2$, and 0.05% NP-40) and supplemented with 5% BSA A 300 µL aliquot of the 1:5 v/v pre-swollen. Protein A beads were incubated overnight at 4° C. with excess immunoprecipitation antibody (typically 5-20 µL, depending on the antibody). The antibody-coated Protein A beads were washed 5 times with ice-cold NT2 buffer and resuspended in 900 µL of NT2 buffer supplemented with 100 U/mL RNase OUT, 0.2% Vanady/Ribonucleoside Complexes, 1 mM DTT, and 20 mM ethylene diaminetetracetic acid (EDTA). The beads were briefly vortexed and 100 µL of the mRNP lysate was added. The beads were immediately centrifuged and a 100 µL aliquot was removed to represent total cellular RNA (essentially one-tenth the quantity of lysate used in the mRNP immuno-precipitations). The immunoprecipitation reaction and an aliquot removed to represent total cellular RNA were tumbled at room temperature for a time period of from zero minutes to two hours. Following appropriate incubation, the Protein A beads were washed four times with ice-cold NT2 buffer followed by two washes with NT2 buffer supplemented with 1 M urea. The washed beads were resuspended in 100 µL NT2 buffer supplemented with 0.1% sodium dodecyl sulphate (SDS) and 30 µg proteinase K and incubated for 30 minutes in a 55° C. water bath. Following proteinase K digestion, immunoprecipitated RNA was isolated with two phenol/chloroform/isoamyl alcohol extractions and ethanol precipitated.

RNase Protection Assays. mRNP complexes were immunoprecipitated from the cell lysate and the bound RNA extracted and assayed by RNase protection using the PharMingen Riboquant assay (Phaminoen, San Diego, Calif.) according to the manufacturer's instructions (45014K). Briefly, extracted RNA was hybridized with excess $^{32}$P-labeled riboprobes generated from templates specific for mRNAs encoding L32, glyceraldehyde-3-phosphate dehydrogenase (GAPDH), several murine Myc-related proteins (template set 45356P) and cyclins (template set 45620P). Non-duplexed RNA was digested by treatment with RNase A+T1. The resulting fragments were resolved by denaturing polyacrylamide/urea gel electrophoresis. Because the length of the riboprobe for each mRNA species was a unique size, all detectable mRNA species in a sample could be resolved in a single gel lane. Protected riboprobe fragments were visualized on a phosphoimaging screen (Molecular Dynamics, Sunnyvale, Calif.) after 24 hours of exposure. Phosphoimages were scanned using the Molecular Dynamics Storm 860 System at 100 micron resolution and analyzed using Molecular Dynamics IMAGEQUANT™ Software (V 1.1) (Molecular Dynamics, Sunnyvale, Calif.).

Figures 4A, 4B:
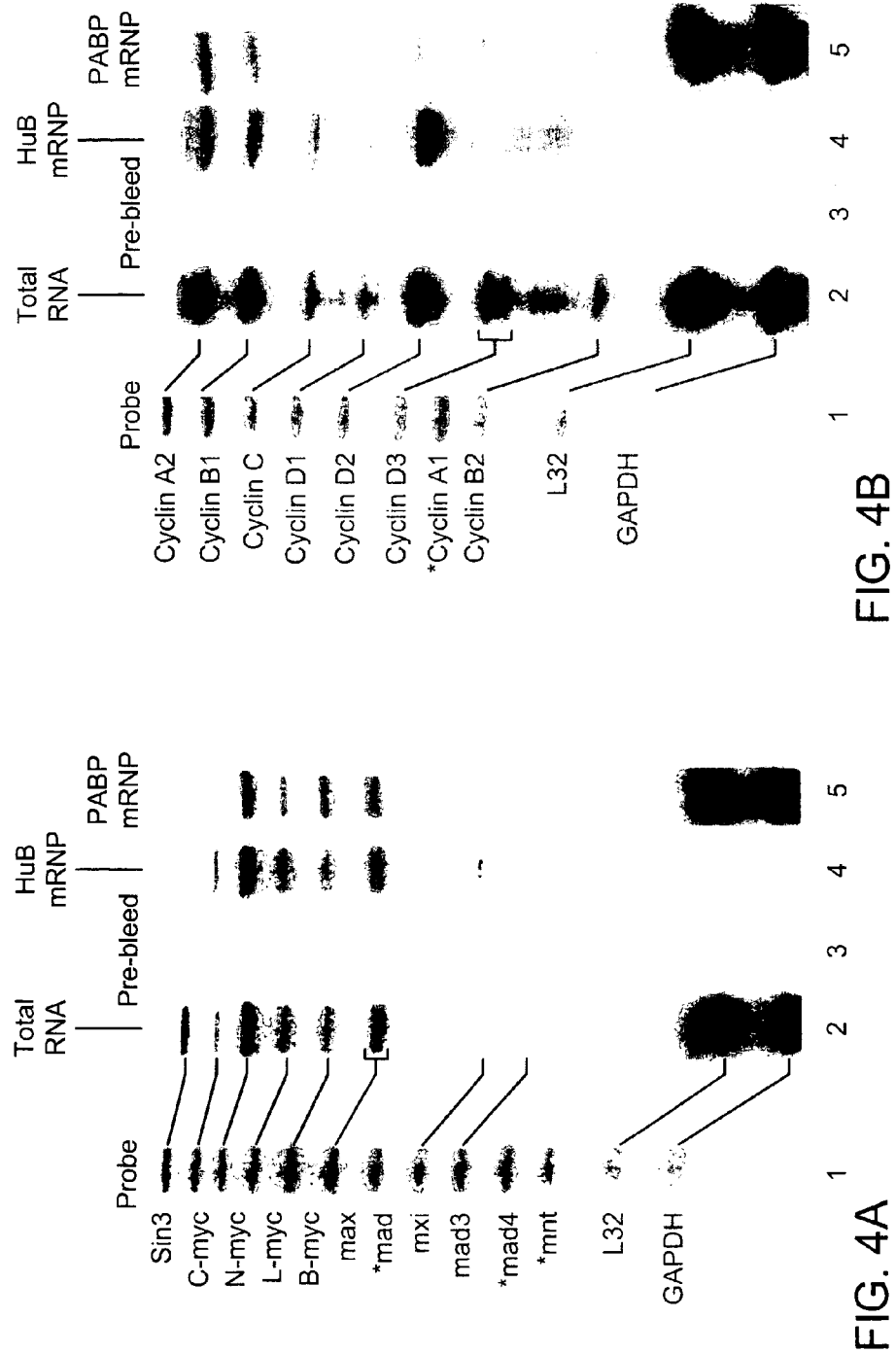
FIGS. 4A and 4B illustrate multiprobe RNase protection analysis of mRNAs associated with mRNP complexes. mRNP complexes from cell lysates were immunoprecipitated and the pelleted RNA was extracted and quantitated by RNase protection.

Results. FIG. 4 shows an immunoprecipitation of HuB and Poly-A binding protein (PABP) mRNP complexes from extracts of murine P19 cells stably transfected with g10-HuB cDNA. No mRNAs were detected in pellets immunoprecipitated with polyclonal pre-bleed rabbit sera (FIGS. 4A and 4B, lane 3), or with any other rabbit, mouse, and normal human sera tested with this assay (data not shown). The profiles of mRNAs associated with HuB mRNP complexes included n-myc, 1-mfc, b-myc, max and cyclins A2, B1, C, D1, and D2, but not sin3, cyclin D3, cyclin B2, L32 or GAPDH mRNAs (FIGS. 4A and 4B, lane 4). In contrast, the profiles of mRNAs extracted from PABP mRNP complexes resembled the profiles of total RNA, but showed enriched levels of L32 and GAPDH and decreased levels of sin3 mRNA (FIGS. 4A and 4B, lane 5). These results are consistent with the postulated role for Hu proteins in regulating post-transcriptional gene expression during cell growth and differentiation.

Example 2

Figure 5:
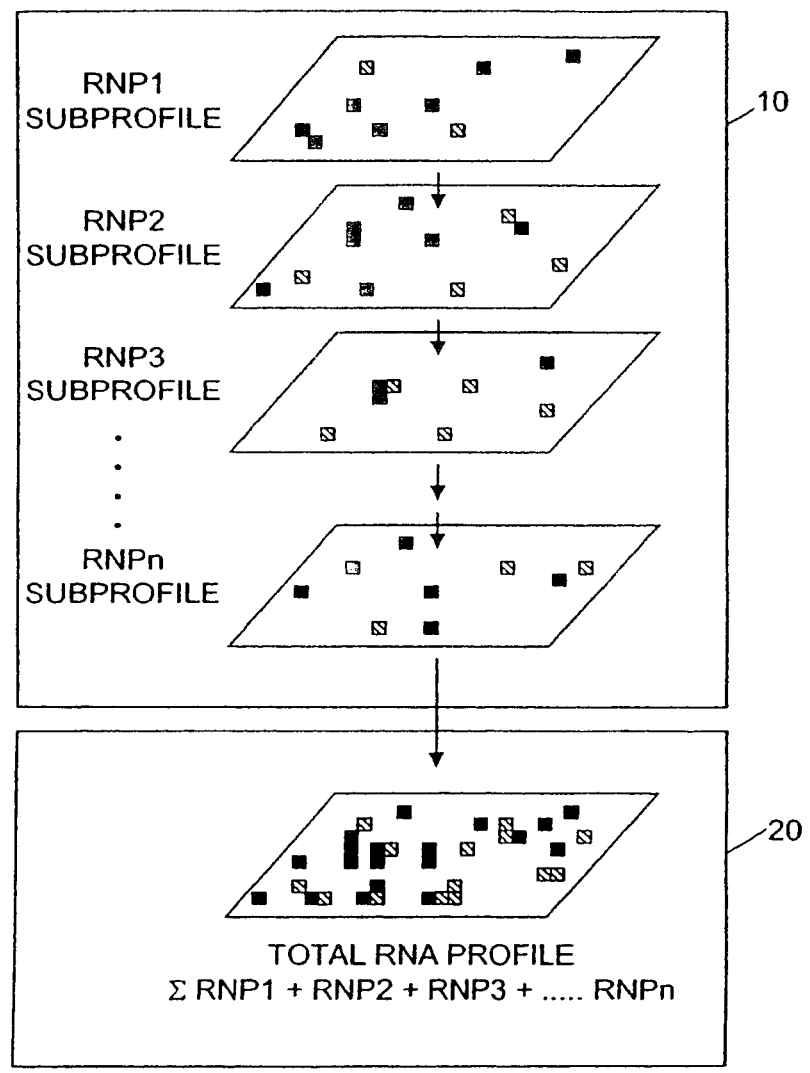
FIG. 5 is a schematic outlining ribonomic profiling of RNA subsets using DNA arrays. The mRNP complexes are isolated from two cell samples (e.g., cells of two individuals, species, cell types, treatments, or developmental stages, for example) and associated RNA pools reverse-transcribed to make RNA probes. A DNA array of genes or cDNAs is probed with each pool of mRNP-derived probes to generate gene expression subprofiles (10). Subprofiles are then compared by subtraction or addition to generate an overall gene expression profile (20). The subprofiles (mRNP1, mRNP2, . . . mRNPn) of the total cell profile are shown as additive. Each stacked subprofile represents individual mRNP complexes within a single cell type, or can represent each individual cell's transcriptome within a complex tissue or tumor.

Identification of mRNA Subsets Associated with RNA Binding Proteins En Masse Using cDNA Arrays A cDNA array (FIG. 5) was used to detect an mRNA subset without amplification or iterative selection.

Antibodies. Monoclonal anti-gene 10 (g10) antibodies and polyclonal sera reactive with the proteins were produced as previously described. Antibody against 5' cap binding protein (e1F-4E) was obtained from Transduction Laboratories (San Diego, Calif.). Antibodies reactive with Poly A-binding protein (PABP) were obtained from McGill University (Canada).

Cell Culture and Differentiation. Transgenic cells were prepared as described in Example 1. Cells were treated with retinoic acid (RA) to induce neuronal differentiation as follows: $5 \times 10^5$ p19 cells were placed on a 60 mm petri dish (Fisher Scientific, Pittsburgh, Pa., Number 8-757-13A) with 0.5 µM RA (Sigma Chemicals, St. Louis, Mo., Number R2625). After two days, 25% of the cells that had formed into clumps were removed, placed in new petri dishes, and supplemented with fresh medium and RA. After two days, cell aggregates were washed once with phosphate-buffered saline (PBS) and trypsinized. The cells were then plated into two 100 mm gelatin-coated tissue culture plates. Cells were harvested after an additional four days. The RA-treated HuB (Hel-N2) stably transfected P19 cells grew neurites and displayed characteristic neuronal markers and morphology, but did not terminally differentiate and remained susceptible to killing with mitotic inhibitors. Cell-free extracts and immunoprecipitations were obtained as described in Example 1.

cDNA Array Analysis. cDNA array analysis was performed using ATLAS™ Mouse Arrays (Clontech, Inc., Palo Alto, Calif.) that contain a total of 597 cDNA segments spotted in duplicate, side-by-side on a nylon membrane. Probing of cDNA arrays was performed as described in the Clontech (Palo Alto, Calif.) ATLAS™ cDNA Expression Arrays User's Manual (PT3140-1). Briefly, RNA was extracted from HuB stably transfected P19 embryonal carcinoma cells and used to produce reverse transcribed probes. A pooled set of primers, complementary to the genes represented on the array, was used for the reverse transcription probe synthesis, which was radiolabeled with $^{32}$Pα-dATP. The radiolabeled probe was purified by passage over CHROMA SPIN™-200 columns (Clontech, Inc., Palo Alto, Calif.) and incubated overnight with an array membrane using EXPRESSHYB™ hybridization solution (Clontech, Inc., Palo Alto, Calif.). Following hybridization, the array membrane was washed and visualized on a phosphorimaging screen (Molecular Dynamics, Sunnyvale, Calif.).

Phosphorimages were scanned using the Molecular Dynamics STORM 860 System at 100 micron resolution and stored as files. Images were analyzed using ATLASIMAGE™ 1.0 and 1.01 software (Clontech, Inc., Palo Alto, Calif.). The signal for any given gene was calculated as the average of the signals at two duplicate cDNA spots. As described in the ATLASIMAGE™ 1.0 software manual (Clontech, Inc., Palo Alto, Calif.), a default external background setting was used in conjunction with a background-based signal threshold to determine gene signal significance. The signal for a gene was considered significantly above background if its adjusted intensity (total signal minus background) was more than two-fold the background signal. Comparisons of multiple cDNA array images were performed using an average of all the gene signals on the array (global normalization) to normalize the signal intensity between arrays. Changes in the mRNA profile of HuB mRNP complexes in response to RA treatment were considered significant if they were four-fold greater (twice the stringency typically used for establishing significance of a gene expression change). cDNA array images and overlays were prepared using ADOBE PHOTOSHOP® 5.0.2 (San Jose, Calif., USA).

Results. After assessing the overall gene expression profile of the HuB transfected P19 cells (the transcriptome), HuB and PABP mRNA complexes, as well as e1F-4E mRNP complexes, were separately immunoprecipitated and captured mRNAs were identified on cDNA arrays. The initial alignment of these arrays was facilitated by spiking the hybridization reaction with radiolabeled lambda phage markers that hybridized with six DNA spots on the bottom of the array membrane. Once the alignment register was established, subsequent blots did not require the use of spiked lambda markers for orientation.

Arrays generated from immunoprecipitations with rabbit pre-bleed sera were essentially blank, with the exception of the spiked lambda markers observed at the bottom of the array (FIG. 6A). Immunoprecipitated HuB mRNP complex and e1F-4E mRNP complexes contained slightly more than 10% of the mRNAs detected in total cell RNA, but differed considerably from one another (FIGS. 6B, 6C, and 6E).

Like HuB and e1F-4E, PABP has been implicated in facilitating mRNA stabilization and translation. Not surprisingly, PABP-associated mRNP complexes contained many more detectable mRNAs than those observed in the HuB or e1F-4E mRNP complexes (FIG. 6D). As expected, the profile of the mRNAs in the PABP mRNP complexes from these cells closely resembled that of the transcriptome. However, as was seen for HuB and e1F-4E mRNP complexes, some mRNAs were enriched or depleted in the PABP-mRNP complexes as compared to the total RNA (FIGS. 6D and 6E). The profiles and relative abundance of mRNAs detected in these mRNP complexes were highly reproducible, but the absolute number of mRNA species detectable on the phosphorimages occasionally varied as a result of differences in the specific activity of the probe.

Because the cDNA arrays derived using total RNA were generated using one-tenth the quantity of lysate used for mRNP complexes immunoprecipitations, a comparison of the absolute quantities of each mRNA detected in mRNP complexes with those observed in the total RNA was not conducted. A more accurate result was obtained by comparing the relative abundance of each mRNA species to each other within each microarray. For example, the relative abundance of the mRNA encoding β-actin and ribosomal protein S29 (FIG. 6, arrows a and b, respectively) is approximately equal in total cellular RNA, but varied dramatically among each of the mRNP complexes. These findings indicated that the mRNA profiles detected for HuB, e1F-4E and PABP mRNP complexes are distinct from each other and from those of the transcriptome.

Example 3

Alterations in mRNP Complexes in Response to Retinoic Acid

Figure 7A:
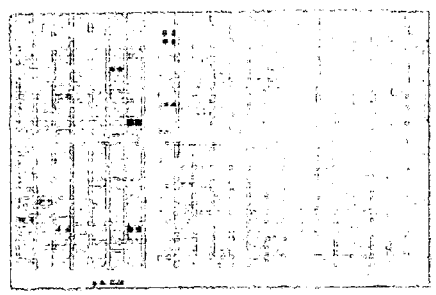
FIG. 7 shows the results of illustrative Example 2 and shows a comparison of the mRNA profiles from HuB and HuA mRNP complexes before and after treatment with retinoic acid. Panels: (A) mRNAs extracted from HuB mRNP complexes immunoprecipitated from untreated cells; (B) mRNAs extracted from HuB mRNP complexes immunoprecipitated from retinoic acid-treated cells; (C) mRNAs extracted from HuA (HuR) mRNP complexes immunoprecipitated from untreated cells; (D) mRNAs extracted from HuA mRNP complexes immunoprecipitated from retinoic acid-treated cells; (E) total complement of mRNAs extracted from untreated cellular lysate; and (F) total complement of mRNAs extracted from retinoic acid-treated cellular lysate.
Figure 7B:
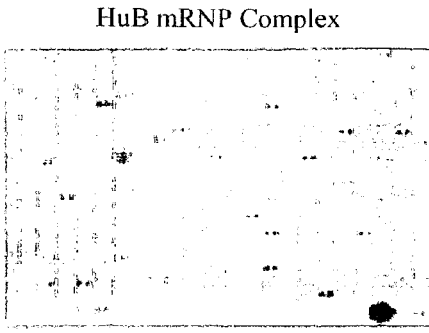
Figure 7C:
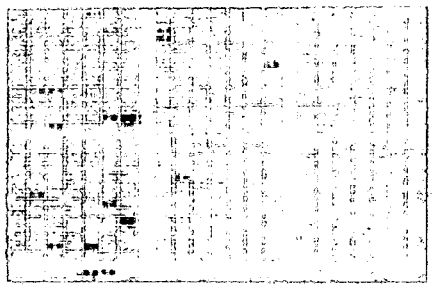
Figure 7D:
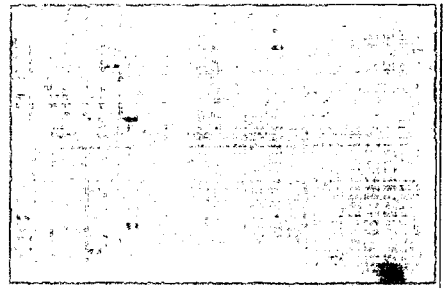

Because HuB is predominantly a neuronal protein believed to play a role in regulating neuronal differentiation, studies were conducted to investigate whether the mRNA population found in HuB mRNP complexes changes in response to RA, a chemical inducer of neuronal differentiation. HuB-transfected P19 cells were treated with RA to induce the onset of neuronal differentiation, HuB mRNP complexes were immunoprecipitated, and then associated mRNAs were identified on cDNA arrays as described in Examples 1 and 2. Comparison of the mRNA profiles extracted from the HuB mRNP complexes before and after RA treatment revealed that eighteen mRNAs were either exclusively present or greatly enriched (four-fold or greater) in RA-treated HuB mRNPs (FIGS. 7A and 7B). In addition, three mRNAs (T-lymphocyte activated protein, DNA-binding protein SATB 1, and HSP84) decreased in abundance by four-fold or greater in response to RA treatment (FIGS. 7A and 7B). To determine if the changes observed in the mRNA profile of the HuB mRNP complexes were unique, the mRNA complexes for the ubiquitously expressed ELAV family member HuA (HuR) was immunoprecipitated from these RA treated cells. Although there were a few changes to the HuA mRNA profile following treatment with the RA, they were minor in comparison with the HuB mRNA profile (FIGS. 7C and 7D).

Figure 7E:
Figure 7F:
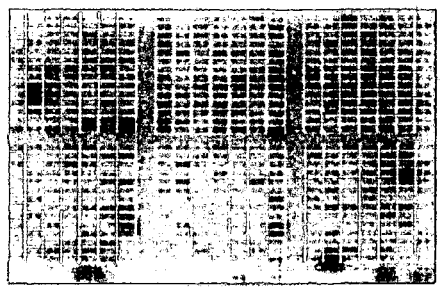
Figure 8:
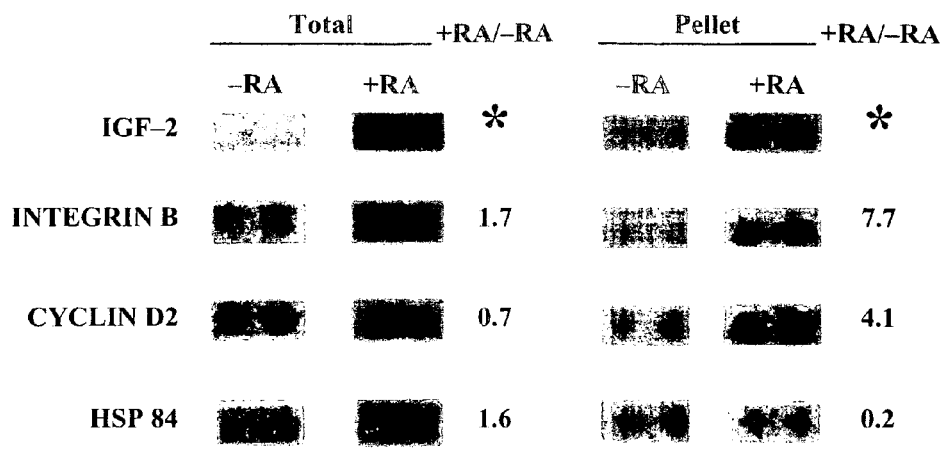
FIG. 8 is a is a comparison of global gene expression profiling with ribonomic profiling. The figure shows representative microarray spots from FIG. 7 that are aligned and enlarged to compare levels of IGF-2, integrin β, cyclin D2, and HSP84 total mRNA with that associated with HuB-bound mRNAs, before and after retinoic acid treatment. Total and HuB-associated IGF-2 mRNA levels increased in response to retinoic acid treatment. By contrast, HuB-associated integrin β, cyclin D2 and Hsp 84 mRNA levels increased or decreased disproportionately to changes in their total RNA levels after RA treatment. *, mRNAs detected only in RA-treated cells.

The changes in the HuB-associated mRNA profile in response to RA treatment did not merely reflect changes in the total cellular mRNA (FIGS. 7E and 7F). However, in some cases, changes in the HuB mRNA profile reflected global changes in the total RNA profile. Numerous examples of differentially-enriched or depleted mRNAs detected in HuB mRNP complexes are evident by comparing FIGS. 7A and 7B to FIGS. 7E and 7F. For comparative purposes, selected examples of mRNAs that demonstrate differences between the total RNA profile in comparison with HuB-bound mRNAs before and after RA treatment are depicted in FIG. 8 by realignment and enlargement of representative spots from the arrays depicted in FIGS. 7A, 7B, 7E, and 7F. For example, IGF2 mRNA was detectable only in total RNA and HuB mRNP complexes from RA treated cells (FIG. 8). However, other HuB mRNP-bound mRNAs, such as integrin beta, cyclin D2, and Hsp84 increased or decreased in abundance disproportionately to their changes in the total RNA profile following RA treatment (FIG. 8). The disparity between changes in the mRNA profiles of total RNA and HuB mRNP complexes possibly results from changes in compartmentalization of mRNAs that flux dynamically through mRNP complexes in response to RA treatment. In conclusion, the mRNA profiles derived from these mRNP complexes are dynamic and can reflect the state of growth, as well as changes in the cellular environment in response to a biological inducer such as retinoic acid.

Example 4

In vivo Target Sequence Preferences for RNA Binding Proteins

Using GenBank and EST databases, the 3' UTR sequences from mRNAs enriched in RA-treated HuB mRNP complexes were identified (TABLE 2). Using the previously defined in vitro binding sequence for HuB, UUUAUUU [SEQ. ID NO: 38], a Basic Local Alignment Search Tool (BLAST®) (National Center for Biotechnology Information (NCBI), Bethesda, MD) analysis and/or visual inspection was performed to identify sequences similar to this consensus binding site within the 3' UTRs of neuronal HuB target mRNAs. Recognizable HuB protein-RNA binding sequences were identified within the in vivo-captured mRNA subset. Many of the mRNAs for which 3' UTR sequences were available contained similar uridylate-rich motifs to those that bind to Hu protein in vitro. Moreover, most of these mRNAs encode proteins that are expressed in neuronal tissues or are up-regulated following RA-induced neuronal differentiation. The sequence alignment shown in TABLE 2 is consistent with the previous results where in vitro selection was used to derive a consensus RNA binding sequence for HuB. Using the methods described herein, it is possible to discern in vivo target sequence preferences for other RNA binding proteins.

TABLE 2

| Gene | #3'UTR Consensus Sequence | |
|---|---|---|
| CD44 | AUUUUCUAUUCCUUUUUUAUUUUAUGUCAUUUUUUUA | [SEQ ID NO: 1] |
| IGF-2 | UAAAAAACCAAAUUUGAUUGGCUCUAAACA | [SEQ ID NO: 2] |
|  | UAAAGAAAUUAAUUGGCUAAAAACAUA | [SEQ ID NO: 3] |
|  | CUAAAAUUAAUUGGCUUAAAAA | [SEQ ID NO: 4] |
| HOX2.5 | UCACUCUUAUUAUUUUAU | [SEQ ID NO: 5] |
|  | AAAUUUUAUUAAGUUA | [SEQ ID NO: 6] |
|  | AUCAGGUUCAUUUUGGUUGU | [SEQ ID NO: 7] |
| Inhibitor | AUUUUAUCUGUUA | [SEQ ID NO: 8] |
| J6 | UUUUGUUUUUCUCCCUUUUUUAGUUUUUUCAAA | [SEQ ID NO: 9] |
| GADD45 | UAUUUUUUUUCUUUUUUUUUUUUGGUCUUUAU | [SEQ ID NO: 10] |
|  | UUAAAUUCUCAGAAGUUUUAUUAUAAAUCUU | [SEQ ID NO: 11] |

TABLE 2-continued

| Gene | #3'UTR Consensus Sequence | |
|---|---|---|
| Nexin 1 | UUCUGUUAAAUAUUUUUAUAUACUGCUUUCUUUUUU | [SEQ ID NO: 12] |
| | AUUUUAUAGUAGUUUUUAUGUUUUUAUGGAAAA | [SEQ ID NO: 13] |
| | AUUUGCCUUUUUAAUUCUUUUU | [SEQ ID NO: 14] |
| Egr-1 | UAUUUUGUGGUUUUAUUUUACUUUGUACUU | [SEQ ID NO: 15] |
| Zif268 | UUUUGUUUUCCUU | [SEQ ID NO: 16] |
| Neuronal-Cadherin | UUUUUAUUUUCUGUAUUUUUU | [SEQ ID NO: 17] |
| | UUUUUUUAAAUUUUUUUAUUUUCUUUUU | [SEQ ID NO: 18] |
| | UUUUUUAUUUCUGUAUUUUUU | [SEQ ID NO: 19] |
| | UUUUUAAUUUUUAAUUUUUUUUU | [SEQ ID NO: 20] |
| Integrin alpha 5 | AAUGGUUUAUAUUUAUGAU | [SEQ ID NO: 21] |
| | UUGUUUAUAUCUUCAAU | [SEQ ID NO: 22] |
| SEF2 | UUCAAGCGCUUGANUU | [SEQ ID NO: 23] |
| Cf2r | UGCAUCGAUCCGUUGAUUUACUACU | [SEQ ID NO: 24] |
| Integrin Beta | UAUAAUUUUUAAUUUUUUAUUAUUUU | [SEQ ID NO: 25] |
| | UUAUUUUACCUUUUUUUUUUUUCUUUAAUUCCUGGU | [SEQ ID NO: 26] |
| CTCF | UUAUGAAUGUUAUAUUUGU | [SEQ ID NO: 27] |
| | UCUUAAUUUUUCUCUUUUUUUCUUU | [SEQ ID NO: 28] |
| TGF beta 2 | UUUUUUUUUCCUUUUAAUUGUAAAUGGUUCUUU | [SEQ ID NO: 29] |
| | UUAAUGAUCAUUCAGAUUGUAUAUAUUUGUUUCCUUU | [SEQ ID NO: 30] |
| | UUCAAUUUUUUUUAUAUACUAUCUU | [SEQ ID NO: 31] |
| | UUUUUC-UUUAAUUGGUUUUUUU | [SEQ ID NO: 32] |
| MTP | UGUCUUGUCUGAGCAUUUAUUUUCAAA | [SEQ ID NO: 33] |
| | UUCUCGUCUUGUUUAUUUUACAA | [SEQ ID NO: 34] |
| | UAUAAUAAUAGUUUAUGUUUUGGAUGUUUGGU | [SEQ ID NO: 35] |
| Cyclin D2 | AUGUCUUGUUCUUUGUGUUUUUAGGAU | [SEQ ID NO: 36] |
| | (AU/GA)UUUAUUU(UA/AG) | [SEQ ID NO: 37] |
| | In Vitro Consensus Sequence | |

Example 5

Target Discovery Using Ribonomic Profiles

Figure 9:
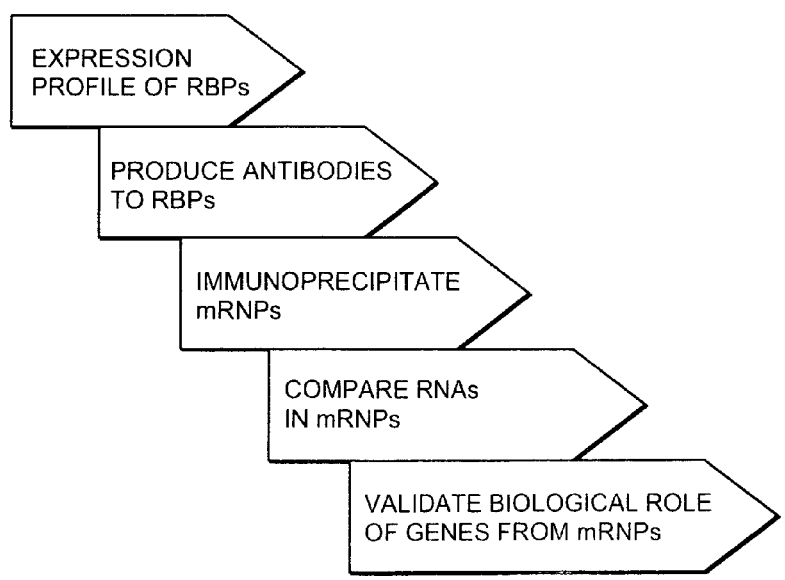
FIG. 9 is a schematic overview of the target discovery process using RNA binding proteins and mRNP complexes.

The steps for target discovery exemplified below are summarized in FIG. 9.

Establishing the expression profiles of RNA binding protein genes. RNA binding protein expression profiles were generated in normal and diseased human tissues. Initial tissue and disease screening of RNA binding proteins was accomplished by Quantitative Reverse Transcriptase-PCR using oligo dT-primers and commercially available RNA samples (Stratagene, Inc., La Jolla, Calif.; Ambion, Inc., Austin, Tex.; BD Biosciences Clontech, Palo Alto, Calif.). 10-100 μg of cDNA was used to perform Quantitative PCR using SybrGreen (Molecular Probes, Inc., Eugene, Oreg.) and gene specific PCR primers on a BioRad iCycler Quantitative PCR machine using protocols provided by the manufacturer. Experimental results were analyzed using the accompanying BioRad icycler software. RNA levels for candidate genes were normalized to rRNA.

For more rapid and comprehensive screening of tissues and cell lines, a custom RIBOCHIP™ spotted microarray (Ribonomics, Inc., Durham, N.C.) was designed and manufactured under contract (MWG Biotech USA, Highpoint, N.C.). A gene list of known and putative human RNA binding protein genes was compiled from a wide variety of public databases and search tools including GenBank (NCBI, Bethesda, Md.), PubMed (NCBI, Bethesda, Md.), SRS Evolution (LION Biosciences, Cambridge, Mass.), LocusLink (NCBI, Bethesda, Md.), Protein FAMily database (pFAM); Welcome Institute Sanger Institute, Hinxton, UK), GO Database (Gene Ontology™ Consortium) and Structural Classification of Proteins (SCOP©) Package (Medical Research Council, Cambridge, UK). This array contained 50 mer oligonucleotides on glass slides corresponding to greater than about 1,400 RNA binding proteins genes in duplicate, non-contiguous positions (plus control genes).

Figure 10:
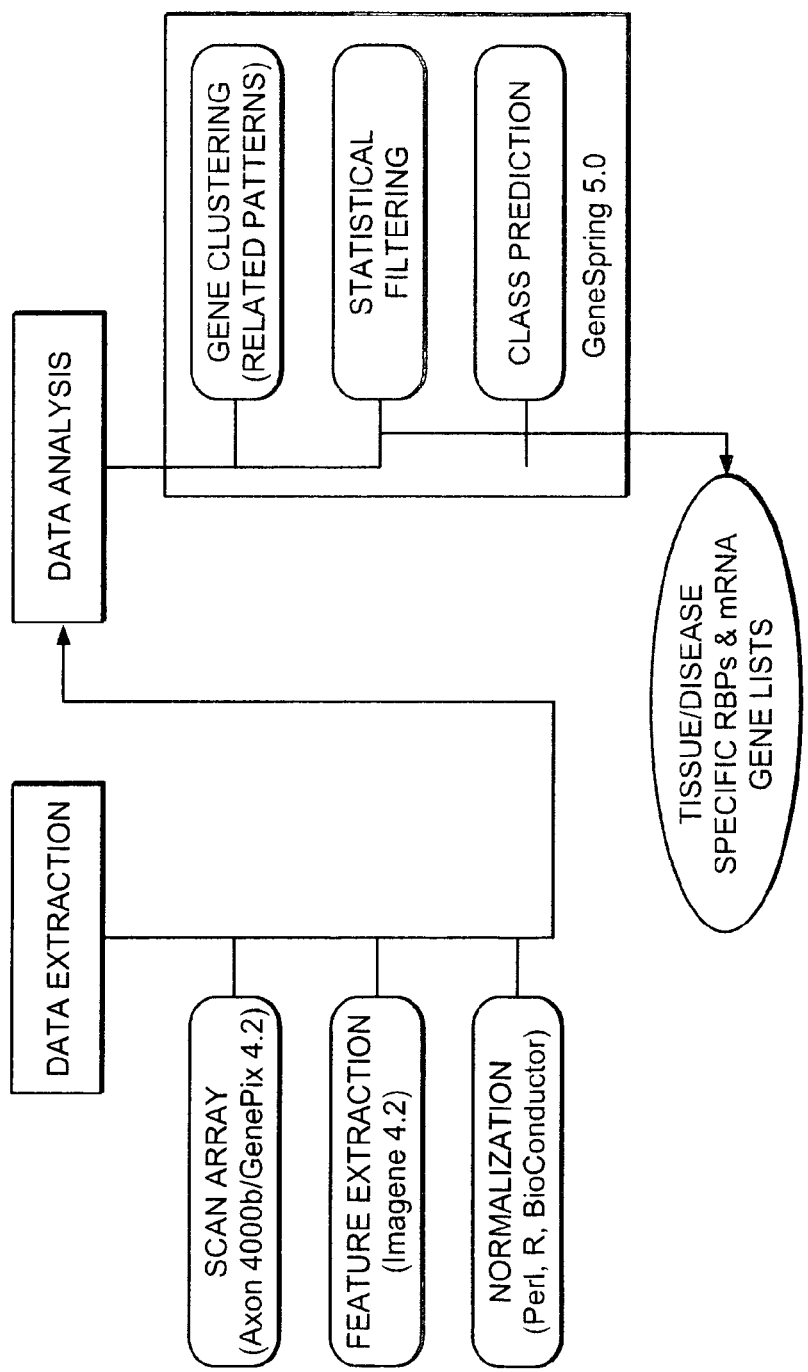
FIG. 10 is a schematic overview of the data flow for analyzing and interpreting microarray results from comparative RNA binding protein expression and/or mRNP complexes.

To screen for the expression of RNA binding proteins, RNA was prepared from cells in culture and from snap frozen clinical tissues according to the Qiagen RNeasy® protocol (Qiagen, Inc., Valencia, Calif.). Total or poly A+ RNA was labeled without amplification through generation of cDNA by reverse transcription in the presence of amino allyl-dUTP followed by direct coupling to Cy3 or Cy5 fluorescent dyes (TIGR SOP#M0004). Hybridization and washing were performed by standard procedures (TIGR SOP#M0005). Data flow for data analysis and statistical analysis is shown in FIG. 10. In short, microarray slides were first scanned and read by a GENEPIX® Axon 4000B scanner using GENEPIX® 4.0 software (Axon Instruments, Inc., Union City, Calif.) for data acquisition. Spot features are then extracted with Biodiscovery's IMAGENE™ V.4.2 package (BioDiscovery, Inc., Marina Del Rey, Calif.). Data preprocessing, including intra- and inter-array data normalization, centralization, and scaling, was accomplished through by visual (e.g., heat map) and quantitative methods (e.g., distribution analysis) implemented using the statistical environment R (Ross Ihaka and Robert Gentleman, R: A language for Data Analysis and Graphics, Journal of Computational and Graphical Statistics, 1996, 5, 299-314; hereby incorporated by reference) and BioConductor Suite of microarray data normalization and analysis libraries (BioConductor, Biostatistics Unit of Dana Farber Cancer Institute, Boston, Mass.). Final data analysis with normalization and scaling was then accomplished using gene clustering, statistical filtering and class prediction functions within the GENESPRING® 4.2.1 software platform (Silicon Genetics, Redwood City, Calif.). Based upon array data, RNA binding proteins that are up or down regulated (e.g., differential RNA binding protein mRNA levels) to a statistically significant extent in a tissue or disease specific manner were selected for confirmation studies by Quantitative PCR, Northern blot and Western blot analyses.

Cloning and Expression of RNA Binding Protein Genes in Bacterial Vectors. As soon as candidate, differentially expressed RNA binding proteins were identified, full length cDNA clones were generated by reverse transcriptase-PCR using commercial RNA tissue sources. Full length plasmid clones were constructed based on phage lambda-based (att) site-specific recombination protocols (Invitrogen, Corp., Carslbad, Calif.) for the GATEWAY™ pENTRD-Topo entry vectors and pDEST17 6XHis destination vectors (Invitrogen, Corp., Carslbad, Calif.). *Escherichia coli* (e.g., BL21 S1 or BL21A1) expressing polyhistidine-tagged RNA Binding Protein fusion proteins were grown to mid-log phase at 37° C. and induced 0.3 M NaCl for BL21SI cells or 0.2% mM arabinose or 0.1 mM IPTG for BL21A1 cells at 20-37° C. for 2-6 hours (based upon optimization in pilot expression studies for each clone). Bacterial cells were lysed by sonication and the fusion protein was purified on nickel columns (Qiagen, Inc., Valencia, Calif.) using standard methods. Insoluble fusion proteins were maintained and purified in the presence of 8M urea, and soluble proteins were maintained in PBS. Purified recombinant proteins were used for immunization of rabbits and/or chickens for production of polyclonal antibodies (typically through contract production). Polyclonal antibodies were characterized for their ability to immunoprecipitate and western blot native and recombinant proteins.

Interrogation of mRNP complexes. RNA binding proteins that are expressed in a tissue or disease specific manner are surrogate markers for cellular alterations due to the post-transcriptional processing of functionally related groups of mRNAs. Changes in the abundance or constellation of RNA binding proteins in a cell undoubtedly affect the processing of any mRNAs bound by those RNA binding proteins. The mRNAs associated with these specific RNA binding proteins are very likely to be critically or causally involved in the phenotype of the cell. Thus, as a subset, those genes whose mRNAs are associated with tissue or disease specific mRNP complexes are a rich source of therapeutic targets for drug discovery.

Figure 11:
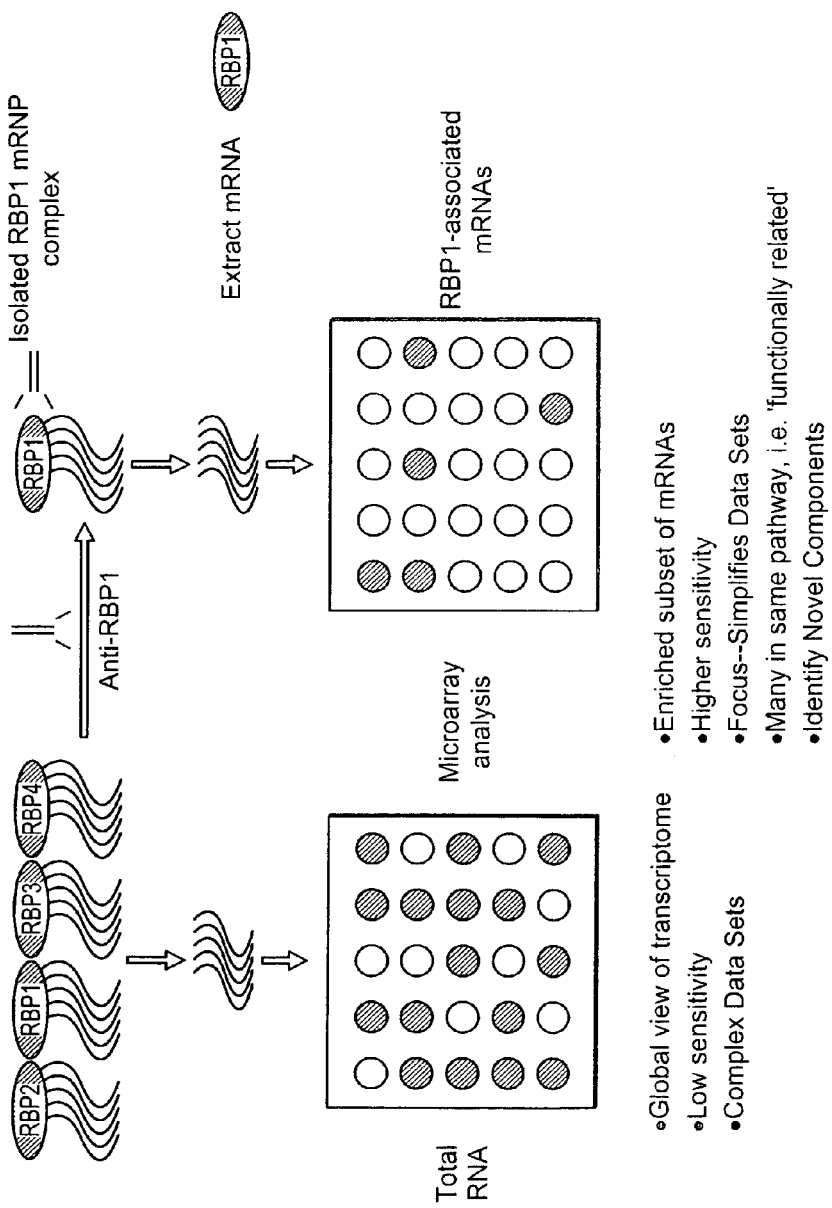
FIG. 11 is a schematic overview of the Ribonomic Analysis System (RAS™) assay compared to microarray analysis of total cellular RNA. otal RNA by microarray analysis

Prioritized RNA binding proteins (e.g., RNA binding proteins that exhibited the most dramatic variations with regard to expression) proceeded into the second stage of analysis, the Ribonomic Analysis System (RAS™) assay (Ribonomics, Durham, N.C.) (FIG. 11). The RAS™ assay is the affinity isolation and characterization of in vivo formed complexes of mRNA and RNA binding proteins or mRNP complex-associated proteins. Antibodies specific to the RNA binding proteins, mRNA complex-associated protein, or tags on RNA binding protein or mRNA complex-associated protein of interest were used to co-immunoprecipitate the RNA binding protein and the associated subset of mRNAs according to the manufacturers instructions. Using polyclonal or monoclonal antibodies raised to the selected RNA binding proteins, or to tags on the RNA binding proteins or mRNA complex-associated proteins, mRNP complexes were isolated from cell or tissue lysates as described below, and optimized for each RNP complex. The extracted RNA was analyzed in a standard microarray format. Variations on the method have included reversible chemical crosslinking with formaldehyde, use of a variety of tags and beaded reagents (cross-linked to synthetic beads, e.g., sepharose), or inclusion of particular concentrations of salt (e.g., NaCl or KCl) or detergent (e.g., NP-40, deoxycholate) based upon pilot studies. For the analysis of mRNAs associated with mRNP complexes, commercially available glass slide arrays (e.g., such as Agilent Human Unigene 14K (Agilent, Palo Alto, Calif.), MWG Pan Human 10K (MWG Biotech, Inc., High Point, N.C.), or membrane arrays, such as Atlas™ Arrays (BD Biosciences, Clontech, Palo Alto, Calif.)), were utilized using protocols for hybridization, washing, and development provided by the array manufacturers.

Preparation of Cell Free Extracts. Composition of the RAS™ assay lysis buffer (RLB) may vary depending upon the binding characteristics of a particular RNA Binding Protein for target RNAs. Basic RLB contained 50 mM HEPES, pH 7-7.4, 1% NP-40, 150 mM NaCl, 1 mM DTT, 100 U/ml RNase OUT, 0.2 mM PMSF, 1 µg/ml aprotinin and 1 ug/ml leupeptin. Variations of these basic components included changes in salt concentrations (0-500 mM NaCl or 0-5 mM KCl), ionic conditions (0-10 mM $MgCl_2$ or 0-20 mM EDTA), and reducing environment (0-5 mM DTT). For example, in order to prepare cell extracts for examining the PTB mRNP, cultured cells were washed in ice-cold PBS and scraped directly into RLB containing 5 mM $MgCl_2$ and incubated on ice for 10 minutes followed by centrifugation at 3,700×g for 10 min at 4° C.

It is necessary in certain cases to crosslink the RNA binding protein to target mRNAs prior to lysis and mRNP isolation. This was performed on cultured cells as well as fresh tissue samples. The extent of crosslinking was titrated for each cell line or tissue and monitored based on ability to immunoprecipitate mRNA in the complex. Cultured cells or tissue were incubated in PBS containing 0-1% formaldehyde at room temperature for 15-60 min. Crosslinking was then quenched by the addition of 1M Tris to a final concentration of 250 mM and incubated further for an additional 20 minutes. The samples were then washed 3×in PBS containing 50 mM Tris. For cultured cells, the pellet was resuspended in Radioimmunoprecipitation (RIPA) buffer (50 mM Hepes, pH 7.4, 150 mM NaCl, 1% NP-40, 0.1% SDS, 0.5% DOC and 100 U/ml RNase Out) at approximately 2 mg/ml final protein concentration. For tissue, the samples were resuspended in RIPA and homogenized with a Polytron to disrupt the tissue. Following the initial lysis, the samples (tissue and cultured cells) were subjected to sonication with a probe sonicator at output setting 6 (Branson 450, Branson Ultrasonics Corp., Danbury, Conn.) two times for 20 seconds each. Between sonications the samples were allowed to cool on ice for 2 minutes. Lysates were then cleared by centrifugation at 3,700×g for 15 min. Subsequently, mRNP isolation as described above was performed.

Immunoprecipitation of mRNP and RNA Extraction. On average, typical final protein concentrations for the cellular lysates were 2 mg/ml. Approximately 2 mg were used for each immunoprecipitation condition. The cleared cellular extracts were incubated with primary antibody (e.g., anti-PTB was used at a final concentration of 10 µg/ml) or a control antibody at equal concentration (e.g., pre-immune or IgG sera at final concentration of 10 µg/ml) for 2 hours at 4° C. A 25 µl aliquot of Protein A Trisacryl (Pierce Biotechnology, Rockford, Ill.) was added and the samples rotated for 1 hour at 4° C. The immune complex was then washed 6×in RLB buffer by adding 1 ml/wash of RLB buffer followed by brief centrifugations in a microcentrifuge for 30 seconds at 5,000 rpm. After the final wash, 50 µl of RNA extraction buffer from the PicoPure™ RNA isolation kit (Arcturus, Inc., Mountain View, Calif.) was added to the beads, vortexed briefly and centrifuged to pellet the beads. The extracted RNA was purified following the PicoPure™ protocol (Arcturus, Inc., Mountain View, Calif.). RNA present in the mRNP complex was then quantified using the RiboGreen™ assay (Molecular Probes, Inc., Eugene, Oreg.).

Amplification of RNA for Microarray Analysis. Since mRNA isolated from mRNP complexes represents only a small subset of total RNA, we amplified the isolated mRNA prior to labeling. Message Amp™ (Ambion, Inc., Austin, Tex.) was used for RNA amplification according to the manufacturers instructions. Two rounds of amplification were performed prior to labeling by random primer polymerization with Cy3 or Cy5-dUTP. Hybridization and washing were performed according to the microarray manufacturers' protocols and as described above. Microarray data acquisition and analysis were performed as described above.

Analysis of mRNP Cluster Microarray Results. In a standard RAS™ analysis (e.g., normal vs. disease, treated vs. untreated), quantitative and qualitative changes in the total RNA content were compared to changes in the mRNP complex. The data obtained was fractionated into four classes: (1) mRNP Transcripts that show comparable quantitative changes in the mRNP complex, (2) RNAs present in the total RNA but not in the mRNP complex, (3) RNAs present in the mRNP complex but apparently absent or below the level of detection in the total, and (4) RNAs that change in the cluster in a quantitatively different manner than in the total RNA analysis. In addition, the RAS™ assay identifies genes represented by class 4 that do not change in total abundance but that are repartitioned within the cell for alternative processing and regulation. As a result, different splice variants may be translated, the mRNA might be transported to and translated at a specific location within the cell, or translation itself might be up or down modulated. The subsets of genes identified within groups 3 and 4 cannot readily be identified by any other currently available approach to characterization of gene expression. Analysis of mRNP complexes reveals mRNAs that are enriched in the complex but otherwise present at sufficiently low levels to be lost to background in the total RNA. For example, in a recent publication looking at mRNAs associated with the Fragile X Mental Retardation Protein (FMRP) complex three genes (KIAA0561-like, Rab3 GDP/GTP exchange protein, and hCT25324/(Celera, Rockville, Md.)) were considered "absent" in the total RNA class and enriched 30-60 fold in the FMRP complex class. Furthermore, this technique identifies genes in a disease or a cellular state whose expression is carefully controlled by the cell, and thus very likely to represent attractive targets for drug discovery. Since one goal of the invention is the identification of drug targets, downstream efforts are focused on target classes that have proven to be tractable targets for small molecule drugs. Specifically, these target classes include nuclear receptors, G-protein coupled receptors, phosphodiesterases, kinases, proteases, and ion channels, among others. Other target classes of therapeutic interest include secreted molecules, extracellular ligands, and phosphatases. Among these gene classes, particularly attractive targets are those with the most restricted systemic expression profile.

Functional Verification of mRNP complexes. For candidate target genes or gene products identified by the RAS™ assay, expression at the RNA and protein levels was confirmed by quantitative PCR and Western blot. Furthermore, the function of an mRNP complex as it relates to the fate of the associated mRNAs, such as stability, degradation or subcellular localization, was explored through a variety of techniques including, but not limited to, confocal microscopy, in situ hybridization, 3-hybrid reporter analysis to confirm ternary interaction between mRNA and the RNA binding protein or mRNP complex-associated protein, and in vitro methods assessing biochemical activities. Such studies were supported by the in vitro demonstration of RNA binding protein binding to specific nucleotide sequences typically found at the 5' or 3' end of the mRNA.

Validation of a Therapeutic Target's Role(s) in Disease or Cellular Phenotype by RNAi. To confirm that a gene identified in a disease specific mRNP complex plays a direct role in the etiology of disease or other phenotype being studied, candidate target genes were chosen for RNAi inhibition studies. For each candidate therapeutic gene, one or more short DNA segments representing the coding sequence of that gene was individually cloned into a plasmid vector in the sense or antisense direction, downstream of a U6 polymerase III promoter or RNAse P RNA H1. Plasmid vectors were constructed that contain two or more short DNA segments of five candidate therapeutic genes in the sense and antisense directions, downstream of a U6 polymerase III promoter or RNAse P RNA H1. Alternatively, one may construct an RNAi by annealing chemically synthesized complementary 22 bp RNAs (Dharmacon, Lafayette, Colo.). Following transfection of the vector or double stranded RNA into cultured cells, phenotypic characteristics were evaluated to determine the effect of inhibiting the expression of the candidate target. In addition, to verify inhibition of gene expression at the RNA and protein levels, Northern blots and Western blots of time course experiments were performed to demonstrate the efficacy and duration of inhibition for the individual genes. Transfections can result in transient expression for one to five days. Alternatively, vectors expressing RNAi can be stably expressed in cultured cells by co-transfection and selection with a dominant selectable marker such as neomycin. As alternatives to the use of RNAi, traditional antisense DNA or vectors expressing dominant negative forms of targets of interest can be used. Antisense and dominant negative genes can be delivered by direct DNA transfection or through the use of virus vectors including, but not limited to, retroviruses, adenoviruses, adeno associated viruses, baculoviruses, poxyiruses, and polyomaviruses. The biological system of study chosen to demonstrate the role of a gene in disease or cellular phenotype is based upon knowledge in the art of the biological system, including a cell culture or animal model system, that mimics relevant biological features (e.g., uncontrolled growth of a tumor cell).

In addition to inhibition of the candidate target genes, RNAi constructs were use to inhibit expression of the RNA binding proteins that bound the mRNAs of the candidate genes. Although inhibition of RNA binding proteins that bind and regulate multiple mRNAs is likely to have a more drastic effect on the phenotype of the cells, this procedure remains an important control to verify the critical importance of the mRNP complex.

Example 6

Discovery and Validation of Novel Targets for Neuronal Differentiation

HuB (Hel-N2) is an RNA binding protein that is believed to play a role in regulating neuronal differentiation. The functional importance of mRNAs in the HuB mRNP complex that are uniquely and critically involved in the differentiation process of p19 cells, an embryonic carcinoma cell line, to a neuronal and glial-like phenotype were identified and validated. As a control, the experiments were duplicated by inducing p19 cells to differentiate into a cardiac and skeletal muscle fate by DMSO treatment.

Cell Culture. G11 cells, which are P19 cells stably transfected with a SV40 promoter-driven pAlpha2-gene 10-HuB plasmid that ectopically expressed a g 10-tagged neuron-specific HuB protein termed Hel-N2, were obtained from Duke University (Durham, N.C.). The transfected plasmid was maintained in the G11 cells by supplementing the medium with 0.2 mg/ml G418 (Sigma Chemicals, St. Louis, Mo.). Parental, untransfected murine P19 cells were obtained from the American Type Culture Collection (ATCC) and maintained in monolayer culture using a-MEM without phenol red supplemented with 7.5% Bovine Calf Serum, 2.5% Fetal Bovine Serum and 100U Penicillin/Streptomycin. Cells were grown in tissue culture flasks or plates that had been pre-coated with 0.1% gelatin that was removed prior to use. Monolayer cell cultures were maintained in 5% $CO_2$ at 37° C.

Neuronal differentiation was induced by treating $5\times10^5$ G11 or P19 cells placed on a 60 mm petri dish with 0.5 μM RA (Sigma-Aldrich, St. Louis, Mo., Catalog # R2625). Muscle differentiation was induced by treating $5\times10^5$ p19 cells placed on a 60 mm petri dish with 5% DMSO (Sigma-Aldrich, St. Louis, Mo., Catalog # D2650). After two days, 25% of the cells that had formed into clumps were removed, placed in new petri dishes, and supplemented with fresh medium and RA or DMSO. Following an additional two days, cell aggregates were washed once with phosphate-buffered saline (PBS) and trypsinized. The cells were then plated into two 100 mm gelatin-coated tissue culture plates. Cells were harvested after an additional four days. The RA-treated G11 cells grew neurites and displayed characteristic neuronal markers and morphology, but did not terminally differentiate and remained susceptible to killing with mitotic inhibitors. The DMSO treated G11 cells displayed characteristic muscle cell markers and morphology, but did not terminally differentiate and remained susceptible to killing with mitotic inhibitors. Cell extracts and immunoprecipitations were performed as described in Example 1. Monoclonal anti-gene 10 (g10) antibodies were obtained from Duke University (Durham, N.C.) as previously described in Examples 1 and 2.

Following immunoprecipitation, the associated mRNAs were identified on high density mouse 12K glass slide microarrays (Mouse cDNA microarray kit, Catalog # G4104A, Agilent Technologies, Palo Alto, Calif.). RNA labeling and microarray analysis was performed according to the manufacturer's protocols (Agilent Technologies, Palo Alto, Calif.). Comparison of the mRNA profiles before and after RA treatment revealed that, in contrast to the approximately 10K genes that were expressed in the total RNA samples, only 1,072 genes were expressed in the G11 HuB mRNP after RA treatment. Further, when the 1,072 genes were broken down into drug-treatable gene classes (e.g., protein classes to which conventional drug therapies are targeted) based on GO (Gene Ontology™ Database) classifications there were 27 kinases (compared to 275 detected in total RNA), 43 phosphatases (compared to 148 detected in total RNA), 14 Proteases (compared to 137 detected in total RNA), 14 Receptors (compared to 87 detected in total RNA), 39 cytokines (compared to 143 detected in Total RNA), and 20 Growth Factors (compared to 87 detected in total RNA) (TABLE 3).

TABLE 3

| Gene Class | # of Genes Detected in Total Cellular RNA | # of Genes Detected in HuB RNP Complex |
|---|---|---|
| Kinases | 275 | 27 |
| Phosphatases | 148 | 43 |
| Proteases | 137 | 14 |
| Receptors | 87 | 14 |
| Cytokines | 143 | 39 |
| Growth Factors | 87 | 20 |

TABLE 4

| Gene | ΔHuB RNP* | ΔTotal Cellular RNA* |
|---|---|---|
| CACN | +14.53X | +1.31X |
| CELSR | +9.41X | −1.33X |
| MBNL | +8.95X | +1.42X |

*Change in amount of RNA for each gene in the HuB RNP or in the total cellular RNA comparing differentiated/undifferentiated in G11 cells at day 1 and day 9.

From five repeat immunoprecipitations, HuB mRNP complex—associated mRNAs were selected that were reproducibly found to be selectively localized to the HuB mRNP complexes with or without substantial changes in the total RNA content in the G11 cells. Among the top 40 genes sorted by largest quantitative increase in the HuB complex, 19 were expressed sequence tags (EST) or Riken clones for which little or no biological information is currently available. Additionally, of those 40, 14 were increased greater than 2×in both the HuB mRNP complex and in the total RNA. Three specific genes were chosen for subsequent analysis: calcium channel beta 3 subunit (CACN), cadherin EGF LAG seven-pass G-type receptor (CELSR), and muscle blind RNA binding protein gene (MBNL) (TABLE 4). The changes in mRNA levels in the HuB mRNP compared to changes observed in the total amount of mRNA in the cell for the three genes are shown in TABLE 4.

Figure 12A:
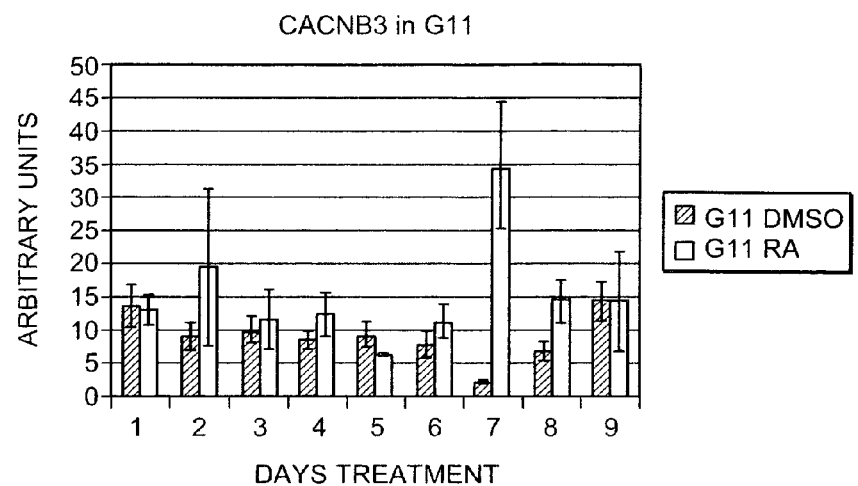
FIGS. 12A, 12B, and 12C show the results of illustrative Example 28 and shows a comparison of the expression profiles of three genes, (A) calcium channel beta 3 subunit (CACN), (B) cadherin EGF LAG seven-pass G-type receptor (CELSR), and (C) muscle blind RNA binding protein (MBNL) in G11 cells, which contain a stably transfected g10-tagged HuB gene, following induction of neuronal differentiation with retinoic acid (RA) and the control condition of muscle differentiation with dimethyl-sulfoxide (DMSO). The expression of these three genes was analyzed by Quantitative RT-PCR during a time course of one to nine days of treatment with either dimethyl-sulfoxide or retinoic acid.
Figure 12B:
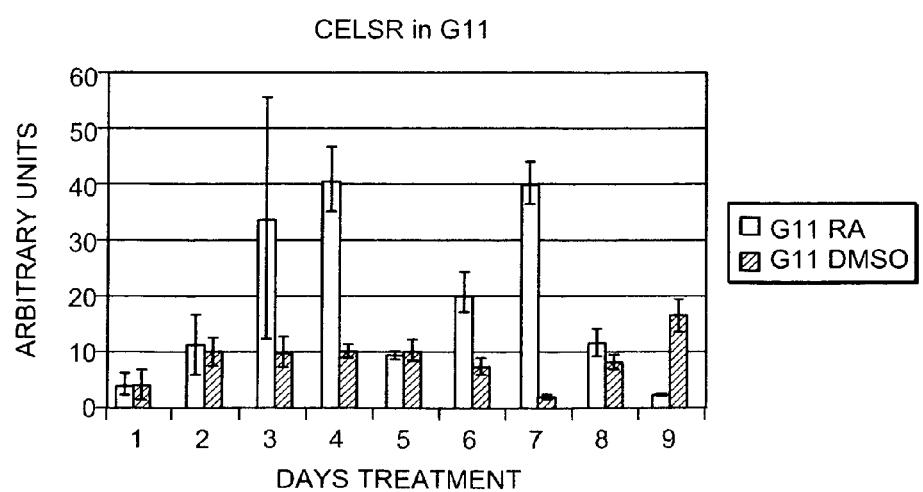
Figure 12C:
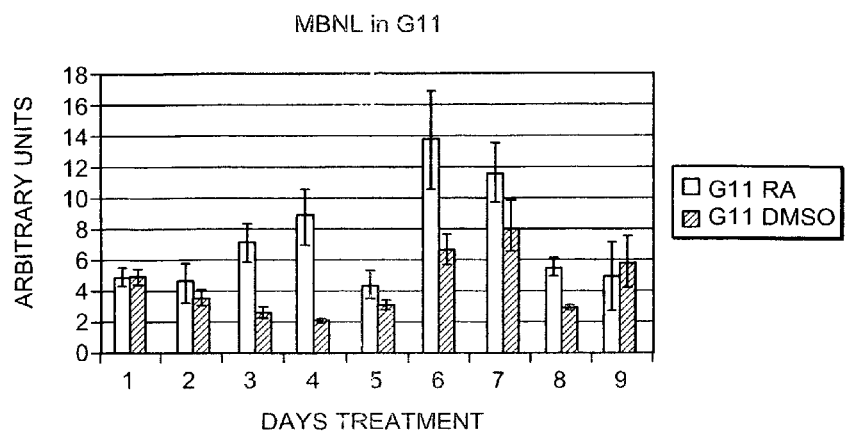

To verify a role in neuronal differentiation, a comprehensive transcriptional analysis by Quantitative PCR was undertaken looking at the patterns of RNA expression for the CACN, CELSR, and MBNL genes in the G11 cells (constitutively expressing HuB) and in the parental P19 cells (FIGS. 12A, 12B, and 12C). For the test cell line, G11, all three genes showed temporal induction over the time course of differentiation following treatment with retinoic acid. In contrast, DMSO induction of G11 cells failed to induce changes in the expression patterns of the same genes, suggesting that, although these genes play a role in neuronal differentiation, expression of these genes is not required for muscle differentiation.

Figure 13A:
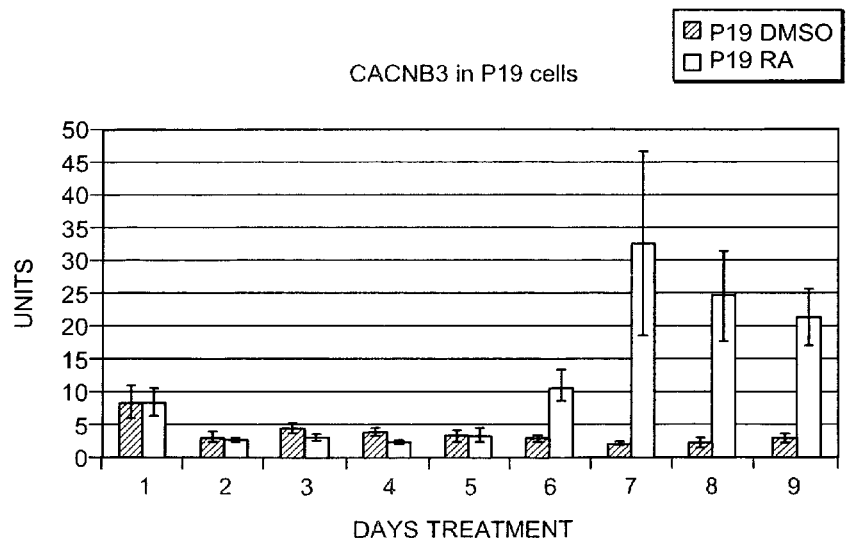
FIGS. 13A, 13B, and 13C show the results of illustrative Example 2 and shows a comparison of the expression profiles of three genes, (A) calcium channel beta 3 subunit (CACN), (B) cadherin EGF LAG seven-pass G-type receptor (CELSR), and (C) muscle blind RNA binding protein (MBNL) in the parental p19 cells following induction of neuronal differentiation with retinoic acid (RA) and the control condition of muscle differentiation with dimethyl-sulfoxide (DMSO). The expression of these three genes was analyzed by Quantitative RT-PCR during a time course of one to nine days of treatment with either DMSO or RA.
Figure 13B:
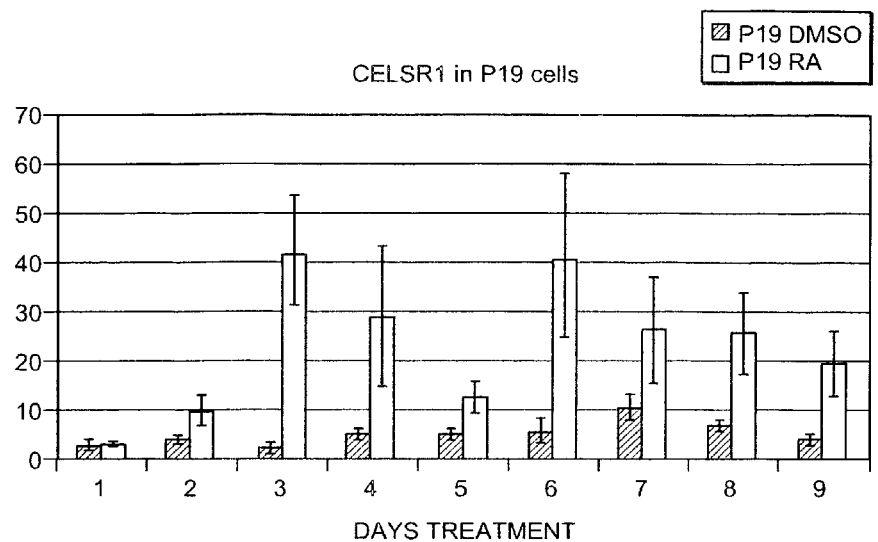
Figure 13C:
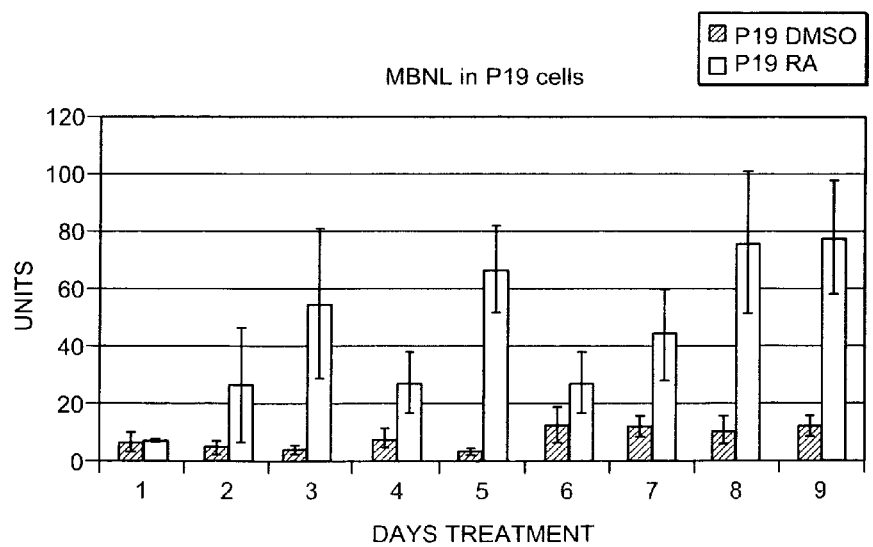
Figure 14:
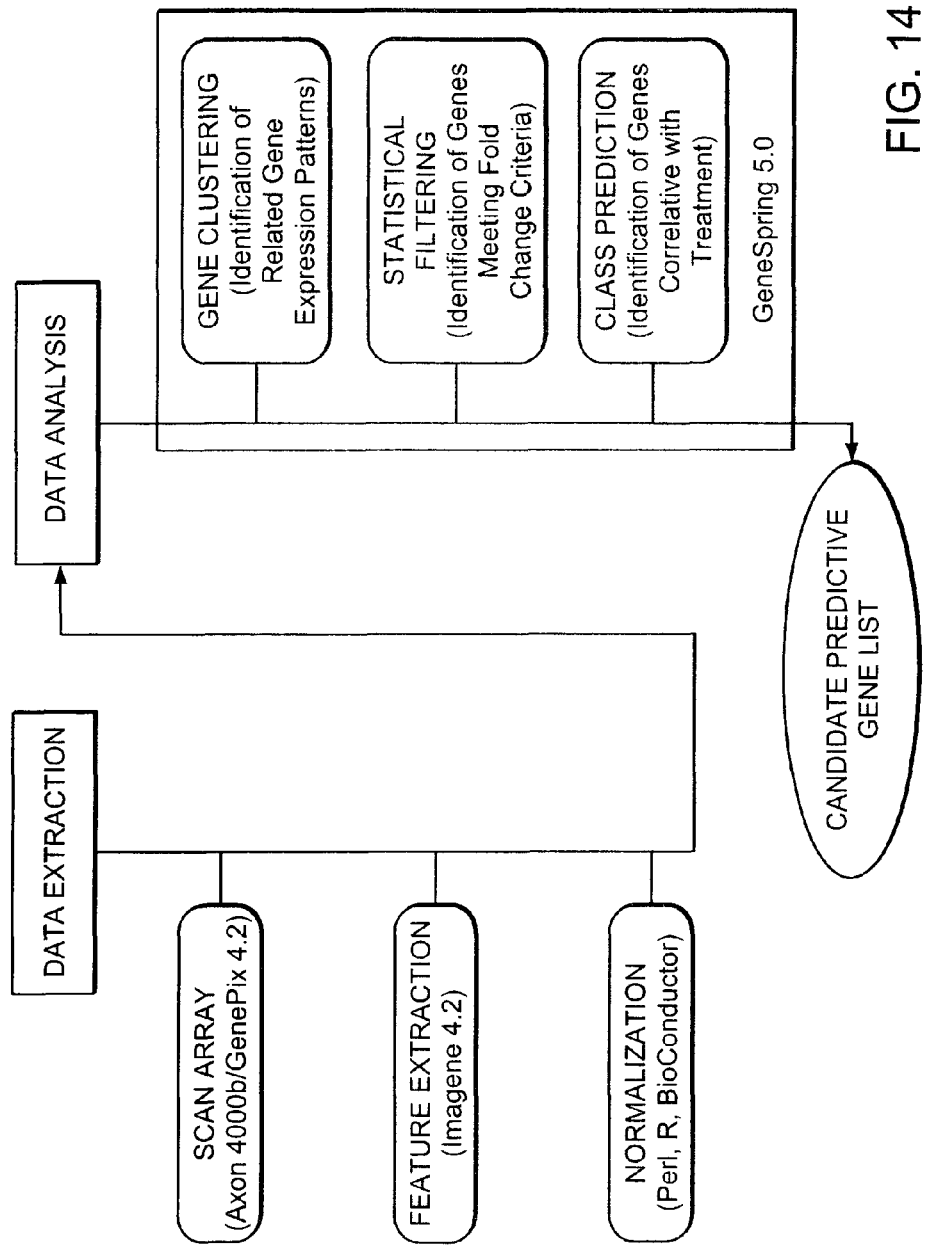
FIG. 14 is a schematic overview of the data flow for analyzing and interpreting microarray results from toxicogenomic studies of RNA binding protein expression profiles.

To further confirm a role for these three genes in neuronal differentiation, expression was examined by Quantitative PCR in the P19 parental cell line lacking the ectopically expressed g10-tagged HuB (FIGS. 13A, 13B, and 13C). Although with slightly varied kinetics, the expression of all three genes is altered over the course of differentiation to neurons, but remains relatively unchanged during differentiation to muscle.

Thus, in the model system of G11 cells, a simple microarray analysis using total RNA samples derived from a comparison of days one and nine would fail to highlight the importance of these three genes in neuronal development. These data are confirmed by the Quantitative PCR levels seen for the G11 cells when comparing day one and day nine samples. However, since they were re-assorted into HuB-containing mRNPs, and since HuB is known to be involved in neuronal differentiation, they were implicated in neuronal differentiation. Such a role is confirmed by the single or dual phase differential expression patterns observed for the three genes between days one and nine in both the test cell line, G11, and more importantly, in the parental cell line, P119. Thus, analysis of critical mRNPs can readily highlight genes that are important in particular biological processes.

Example 7

Screening of RNA Binding Proteins as Sentinels of Hepatoxicity

The human cell line HepG2 was used as a model for hepatotoxicity. HepG2 cells were treated with test compound doses and effects on RNA binding protein gene expression were assessed. Doses that produced 50% mortality 72 hours post-treatment were used to treat HepG2 cells for 24 hours, at which time the effects on gene expression were determined. By using a 24 hour time point for assessing gene expression, it was possible to examine changes in gene expression elicited by compound doses that lead to significant cell death.

Preliminary dose response curves were generated to determine a Highest Tolerated Dose (HTD), the concentration of test compound that produced the minimum detectable morphological changes in the cells (e.g., rounding, vesiculation, detachment, lysis). Briefly, cells were seeded into 96 well tissue culture plates at $2 \times 10^4$ cells/well in Dulbecco's Modified Eagle's Medium (DMEM) with 10% FCS. Twenty-four hours after seeding, the media was removed and fresh DMEM containing 0.1% BSA without FCS and either 0.25% Dimethyl Sulfoxide (DMSO) or 0.25% DMSO, in addition to dilutions of test compound, were added to the cells. For example, dilutions ranging from 4 μM to 10 mM were used for the compounds Clofibrate, DEHP, Gemfibrozil, Phenytoin, and Acetaminophen (Sigma-Aldrich, St. Louis, Mo.).

Twenty four hours after dosing, the cells were assessed visually for morphological changes. The HTD was used to define a narrower dose range to be used in a vital dye cell viability assay (e.g., Alamar Blue, MTT (Roche Applied Science, Indianapolis, Ind.), XTT (Roche Applied Science, Indianapolis, Ind.)). For the vital dye assays, cells were seeded and dosed as described above for 72 hours rather than 24 hours. The 72 hour vital dye toxicity assessment data was used to determine $TD_{50}$ values for each compound, i.e., the Toxic Dose producing about 50% cell death relative to DMSO treatment alone.

The concentration of test compound producing 50% cell death following a 72 hour cell treatment was used to dose cells for mRNA analysis. Cells were seeded into T150 plates at about 20% confluency (equivalent density to that used in $TD_{50}$ determinations) in DMEM with 10% FCS for 24 hours. The medium was removed and replaced with fresh medium containing DMEM and 0.1% BSA (i.e., without FCS) and DMSO alone or test compound and DMSO at the determined $TD_{50}$ concentration. Cells were harvested 24 hours after dosing. Total RNA was extracted from fresh or snap frozen cell pellets using the Qiagen RNeasy protocol (Qiagen, Inc., Valencia, Calif.). Total RNA was quantified by spectroscopy. Integrity was verified by separation on the Agilent Bioanalyzer 2100 (Agilent, Palo Alto, Calif.). Total RNA was labeled without amplification through generation of cDNA by reverse transcription in the presence of amino allyl-dUTP followed by direct coupling to Cy3 or Cy5 fluorescent dyes (TIGR SOP#M0004). The labeled RNA was analyzed using a custom spotted oligonucleotide microarray containing approximately 1400 RNA binding proteins (MWG Biotech, High Point, N.C.). For initial screening, a RiboChip™ V.1.0 microarray (Ribonomics, Durham, N.C.) was used. The RiboChip™ (Ribonomics, Durham, N.C.) was composed of oligonucleotides complementary to greater than 1400 RNA Binding Protein genes plus controls. Alternatively a RiboChip™ microarray (Ribonomics, Durham, N.C.) may also include a comprehensive collection of transcription factors to represent the full set of sentinel genes for the quantitative and qualitative assessment of toxicity. Hybridization of labeled probe and washing were by standard procedure (TIGR SOP#0005).

Figure 15:
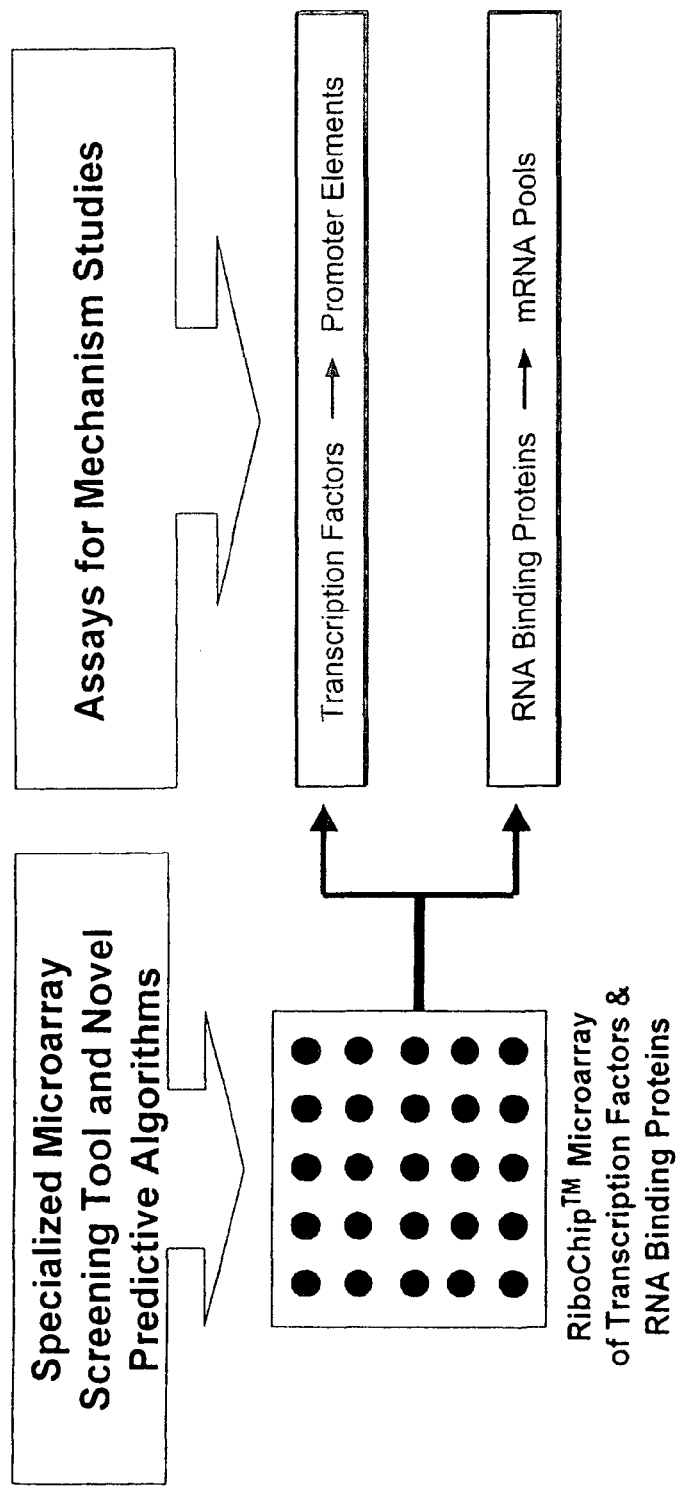
FIG. 15 depicts the use of transcriptional regulators (transcription factors and RNA binding proteins) in mechanism-of-action studies. Expression profiling by microarray analysis of transcription factors and RNA binding proteins (RBPs) using the RiboChip™ microarray is useful for assessing the potential toxicity or for determining the mechanism-of-action studies of drugs or therapeutics. Transcription factors and RNA binding proteins represent 'sentinel regulators' of all gene expression changes. In the case of transcription factors, mechanism-of-action studies include studying the transcription factor binding elements in promoter regions of regulated genes. In the case of RNA binding proteins, the mechanism-of-action studies include studying the mRNA pools that are bound endogenously by particular RNA binding proteins.

Data flow for data analysis and statistical analysis is shown in FIG. 15. In short, microarray slides were first scanned and read by a GENEPIX® Axon 4000B scanner using GENE-PIX® 4.0 software (Axon Instruments, Inc., Union City, Calif.) for data acquisition. Spot features are then extracted with Biodiscovery's IMAGENETM V.4.2 package (BioDiscovery, Inc., Marina Del Rey, Calif.). Data preprocessing, including intra- and inter-array data normalization, centralization, and scaling, was accomplished through by visual (e.g., heat map) and quantitative methods (e.g., distribution analysis) implemented using the statistical environment R (Ross Ihaka and Robert Gentleman, R: A language for Data Analysis and Graphics, Journal of Computational and Graphical Statistics, 1996, 5, 299-314; hereby incorporated by reference) and BioConductor Suite of microarray data normalization and analysis libraries (BioConductor, Biostatistics Unit of Dana Farber Cancer Institute, Boston, Mass.). Final data analysis with normalization and scaling was then accomplished using gene clustering, statistical filtering and class prediction functions within the GENESPRING® 4.2.1 software platform (Silicon Genetics, Redwood City, Calif.) to identify highly predictive gene sets unique to individual compounds, compound classes, and general toxic responses.

These predictive gene sets served as the basis by which to assess changes in gene expression profiles of HepG2 cells elicited by unknown test compounds and as a means to predict and classify hepatotoxicity caused by these compounds (Example 9). In addition, these data are used to predict toxicity in other tissues. Changes in gene expression in HepG2 cells in response to exposure to a test compound were compared to an internal database of gene expression information for a large collection of normal tissues. RNA binding protein genes with expression patterns that are perturbed upon test compound treatment in HepG2 cells are used to predict toxicity of the compound tissues that express that RNA Binding Protein. For example, if a compound elicits a change in expression of a gene uniquely expressed in normal cardiac tissue, then the compound are flagged as having potential for cardiac toxicity.

Example 8

Determining the Mechanism of Toxicity or Mechanism of Action of a Compound by Characterizing mRNP Complexes To validate the mechanistic connections between altered transcriptional regulators and downstream phenotypic effects, the identification of transcription factors and RNA Binding Proteins whose expression is consistently altered in the presence of specific toxicants lead to the identification of downstream genes affected by changes in these transcriptional regulators.

Figure 16:
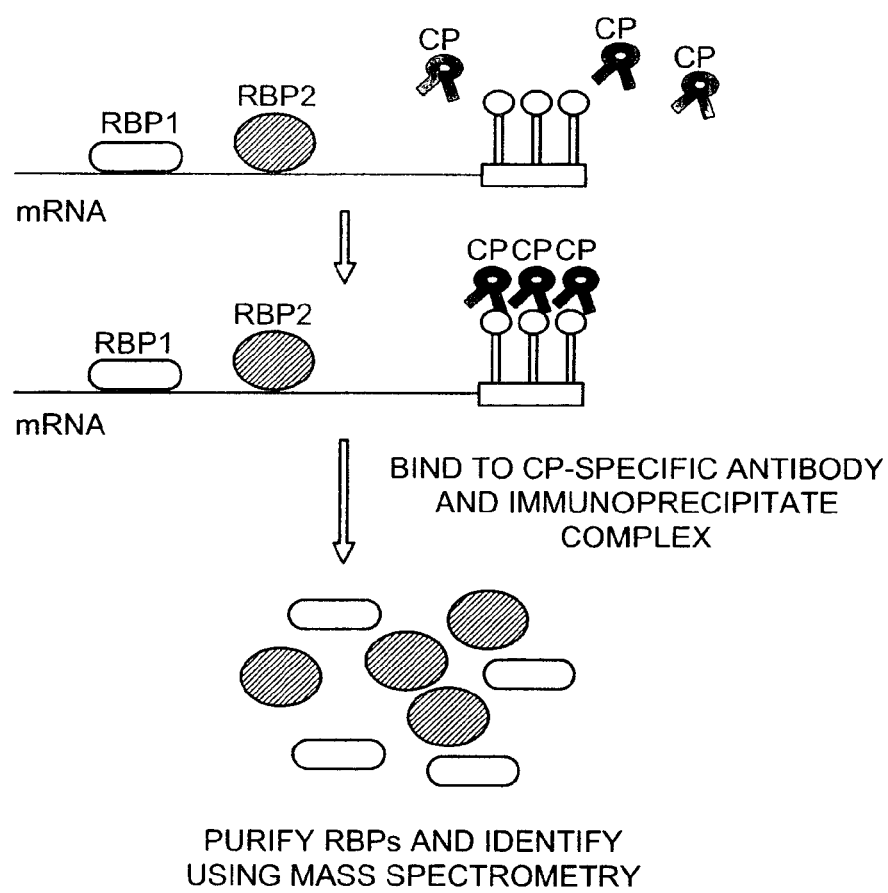
FIG. 16 is a schematic overview of the RiboTrap™ assay. An mRNA encoding an RNA binding protein (RBP1 or RBP2) of interest tagged with a ligand such as MSII coat protein (CP) binding site (RNA stem loops) is introduced into a cell by transfection and expressed. The tag allows for recovery of the mRNA with its attached RNA binding protein. A binding partner for the ligand such as CP antibody is used to immunoprecipitate the tagged mRNA and its associated RNA binding proteins.

One of the most valuable components associated with the use of transcription factors and RNA binding proteins as sentinels of toxicity derives from their subsequent value for providing mechanistic insights and studies (FIG. 16). The consistent up-regulation of a transcription factor or RNA binding protein by a toxicant is very likely to result in downstream effects on genes regulated by these regulators. Such genes can be provisionally identified due to the occurrence of transcription factor binding sites in cis regulatory elements upstream of the coding region of the gene. The DNA binding activity of individual transcription factors can be readily evaluated in toxicant treated cell lysates by in vitro gel retardation assays which measure the ability of a protein to bind to a target DNA sequence and retard its migration during gel electrophoresis. Alternatively, chromatin immunoprecipitation coupled to microarray analysis may be used to identify transcription factor bound segments of DNA. Functional assessment of the regulatory effects of transcription factors is routinely accomplished with the use of reporter gene assays in which one or more copies of the transcription factor binding site is inserted upstream of a reporter gene, typically a foreign enzyme (e.g., β-galactosidase, chloramphenicol acetyl transferase, or a fluorescent molecule such as green fluorescent protein (GFP)). In these assays, changes in gene expression are quantitatively reported through changes in enzymatic activity or fluorescent intensity. Thus, identification of toxicant-regulated transcription factors can be readily assessed through the use of relatively standard laboratory techniques to downstream, mechanistic effects on collections of cellular genes.

The role of RNA binding proteins in the collection, organization, and coordinate processing of associated mRNAs is potentially a rich source of information about downstream toxic effects mediated through particular genes. Since RNA binding proteins bind to conserved sequence elements in the 5' and 3' UTRs of genes to regulate stability, transport, translation, and modulation of the expression of the RNA binding proteins genes themselves, they will have effects on multiple downstream genes. For example, the RNA binding protein tristetraprolin (TTP) binds to AU-rich elements in the 3'UTR of TNF-α and GM-CSF resulting in accelerated degradation of those mRNAs. Furthermore, mice deficient in TTP develop severe pathology consistent with broad autoimmune disease including arthritis, dermatitis, myeloid hyperplasia, and cachexia, symptoms that can be abated by neutralization with antibodies to TNF-α. In a somewhat similar fashion, the congenital absence of another RNA binding protein, FMRP is the primary cause of fragile X syndrome in humans, the most prevalent form of hereditary mental retardation. FMRP binds and localizes a subset of mRNAs to the neuronal synapse to enable localized protein translation in response to neurotransmitters. The absence of the FMRP is thought to cause deregulation of a collection of mRNAs critical for synaptic transmission.

By defining RNA binding protein genes demonstrably up-regulated by a class of compounds, the mRNA pools associated with these RNA binding proteins can be identified. RNA binding protein genes that are regulated by a class of compounds can be cloned and expressed as GST or 6×His tagged fusion proteins using standard cloning procedures and commercial expression vectors. Using bacterial expression vectors, the RNA binding proteins can be expressed either in *E. coli* or in coupled in vitro transcription translation systems. Following incubation and attachment of the recombinant proteins to nickel or GST beads that specifically bind the GST or 6×His tagged proteins, total RNA preparations from compound-treated cells can be added to the RNA binding protein: beads to permit binding of mRNAs from the HepG2 cells. In this manner, those cellular mRNAs which are likely to be associated with the regulated RNA binding protein in liver cells, and likely to be aberrantly affected by drug treatment, can be identified by standard microarray analysis as described above.

Alternatively, depending on the availability of antibodies specific to the RNA binding proteins modulated by drug treatment, endogenous mRNP complexes from HepG2 cells can be immunoprecipitated and the mRNA subsets interrogated as described above. The use of RNA binding proteins altered by compounds will identify pools of mRNAs that could be differentially and coordinately regulated in some aspect of splicing, nuclear transport, stability, subcellular localization, or translation of groups of genes with common functions important for the mechanism of action of a compound class.

Example 9

Isolation of Discrete mRNP Complexes from Cells and Tissues in order to Identify the Full Set of Associated RNA Binding Proteins and RNA Associated Proteins with an mRNA of Interest An alternative and highly directed method called the RiboTrap™ assay (Ribonomics, Durham, N.C.) is used to detect RNA binding proteins and mRNP complex-associated proteins that are associated endogenously with disease-related mRNAs in vivo. The assay defines the constellation of mRNAs that are co-regulated with a gene of interest, such as a drug target. The information obtained can provide novel pathway information for validated targets, additional therapeutic targets for alternative or multi-drug therapies, and surrogate disease markers for monitoring in clinical trials.

Using standard recombinant DNA and PCR technologies, a cDNA representing the gene of interest and/or its 5' and 3' UTRs is constructed. The 3' UTR of the cDNA has a series of repeats of the stem-loop representing the RNA binding site of the phage MS2 coat protein (FIG. 16). Alternatively, any RNA stem loop or other RNA structure that is known to bind a specific protein (e.g., HIV RRE and the Rev protein) could be used.

For prototype experiments, a c-myc cDNA is used because the corresponding mRNA is a binding target of ELAV/Hu proteins both in vitro and in vivo. The c-myc cDNA is cloned into an expression vector possessing an appropriate mammalian cell promoter such as CMV, SV40 or actin promoters, or alternatively an adenovirus or retrovirus vector, and transfected into compatible mammalian cell line. For example, the cDNA encoding a neuronal protein is expressed in a neuronal cell line such as PC12 (rat), P19 (mouse), or hNT2 (human). Alternatively, for a metabolic study, the cDNA is expressed in a preadipocyte (mouse 3T3 μl) or a human adipocyte line.

Following expression of the engineered c-myc cDNA, a cell extract is prepared to fish out the c-myc mRNA containing the MS2 coat protein-binding site. MS2 coat protein is linked to agarose or Sepharose beads or another suitable solid matrix. Antibody to MS2 coat protein or biotinylated MS2 coat protein may also bind to Strepavidin beads. These reagents allow isolation from the cell extract of the mRNA containing the MS2 stem-loop repeats and the RNA binding proteins and/or mRNA complex-associated proteins that are associated with the mRNA in vivo.

Variations on the method include chemical crosslinking with formaldehyde or the use of a variety of tags and beaded reagents. Proteins that are isolated in association with the mRNA of interest using the RiboTrap™ assay (Ribonomics, Durham, N.C.) can be identified using standard proteomic methods. For example, Matrix Assisted Laser Desorption/

Ionization—Time-of-Flight Mass Spectrometry (MALDI TOF) and Tandem Mass Spectrometry (or Mass Spectrometry/Mass Spectrometry (MS/MS)) can be used to identify peptide sequences for database searches. Antibodies reactive with identified proteins can be raised according to standard methods and used to perform the RAS™ assay as described previously.

Following application of the RAS™ assay (Ribonomics, Durham, N.C.), the subpopulation of mRNAs that are present in mRNP complexes can be identified and examined for the presence of common UTR sequence elements. It should be noted that computational analysis for homology is not a reliable method for identifying Untranslated Sequence Elements for Regulation Codes (USER codes) because they are often structural rather than single stranded. More importantly, the subpopulation of mRNAs can be examined for functional relationships. For example, each mRNA can be categorized by gene annotation and by known functions in functional genomics databases (e.g., Locus Link (NCBI, Bethesda, Md.), GO Database (Gene Ontology™ Consortium), Proteome BioKnowledge® Library (Incyte Genomics, Inc., Palo Alto, Calif.)). For example, if the protein used in the RiboTrap™ assay (Ribonomics, Durham, N.C.) is involved in immune regulation, the other mRNAs found in the same mRNP complex can be analyzed for their role in immune regulation. However, the mRNA could be bound indirectly through a different RNA binding protein in the mRNP complex (e.g., is assessed to the presence of USER code element in its UTR that recognizes the RNA binding protein or other known binding sites for RNA binding proteins.

The goal of the RAS™ assay is to identify mRNA populations in which the mRNAs have related structural features in their UTRs or the proteins encoded by the mRNAs have functional relationships. Among the related functions that are expected are a) involvement of encoded proteins in a common metabolic pathway, b) encoded proteins that are temporally co-regulated, c) encoded proteins that are similarly localized in or on the cell, d) encoded proteins that play a role in forming or regulating a biological machine (e.g., a ribosome). The identification of complex traits and phenotypes that result from the expression of a set of functionally-related proteins would include such processes as cognition, cell-specific activation, inflammation, or differentiation. While proteins known to be involved in these complex processes are known from other studies, the majority of the functions remain largely unknown. One of the values of the invention is for discovering a larger set of proteins involved in these processes that could serve as alternative drug targets or surrogate markers.

The invention may be embodied in other specific forms without departing from the spirit or essential characteristics thereof. The foregoing embodiments are therefore illustrative rather than limiting of the invention described herein. The invention is described by the following claims, with equivalents of the claims to be included therein.

We claim:

1. A method of evaluating an effect of a test compound on an endogenous RNA subset associated with an mRNA-protein (mRNP) complex in a cell comprising an endogenous RNA binding protein (RBP), endogenous mRNP complex associated protein, or an endogenous RNA associated protein (RAP), the method comprising the steps of:
   a) exposing the cell to the test compound;
   b) lysing the cell exposed to the test compound to produce a lysate;
   c) contacting the lysate with a ligand that specifically binds at least one component of the mRNP complex, wherein the mRNP complex is bound by the ligand;
   d) partitioning the mRNP complex bound by the ligand to a solid support;
   e) removing the mRNP complex bound to the ligand and the solid support from the lysate;
   f) identifying and, optionally quantifying, the endogenous RNA subset from the removed mRNP complex without amplifying the RNAs by PCR, wherein the identified RNAs of the endogenous RNA subset are encoded by a plurality of distinct genes; and
   g) comparing the identified RNAs of step f) with the RNAs from a control RNA subset, and optionally the levels of one or more RNAs in step f) to the levels of the one or more RNAs in the control RNA subset, from the mRNP complex generated by performing steps b-f on a control cell, wherein the control cell is of the same type as the test cell and is not exposed to the test compound;
   thereby evaluating the effect of the test compound on the identity, and optionally the quantity, of the endogenous RNA subset.

2. The method of claim 1, wherein the ligand is an antibody.

3. The method of claim 2, wherein the at least one component of the mRNP complex to which the antibody binds is the endogenous protein.

4. The method of claim 1, wherein the at least one component of the mRNP complex, to which the ligand specifically binds, is an RNA from the RNA subset.

5. The method of claim 1, wherein the at least one component of the mRNP complex, to which the ligand specifically binds, is an RAP.

6. The method of claim 1, wherein the cell is a diseased cell.

7. The method of claim 6, wherein the diseased cell is a tumor cell.

8. The method of claim 6, wherein the diseased cell is a cell infected with a pathogen.

9. The method of claim 6, wherein the test compound is a drug used in the treatment of the diseased cell.

10. The method of claim 1, wherein the test compound is a drug.

11. The method of claim 2, wherein the test compound is a drug.

12. The method of claim 1, wherein the step of identifying in step f) further comprises determining the amount of the endogenous proteins from the RNP complex.

13. The method of claim 1, wherein the endogenous RNA subset is identified en masse.

14. A method of evaluating an effect of a test compound on an endogenous RNA subset associated with an mRNP complex in a cell comprising an endogenous RBP, endogenous mRNP complex associated protein, or an endogenous RAP, the method comprising the steps of:
   (a) exposing the cell to the test compound;
   (b) expressing an epitope-tagged ligand in the cell exposed to the test compound, said ligand being a component of the mRNP complex;
   (c) lysing the cell to produce a lysate comprising the mRNP bound to the epitope-tagged ligand;
   (d) partitioning the mRNP complex bound to the epitope-tagged ligand to a solid support;
   (e) removing the mRNP complex bound to the ligand and the solid support from the lysate;
   (f) identifying and, optionally quantifying, the endogenous RNA subset from the removed mRNP complex without amplifying the RNAs by PCR, wherein the identified RNAs of the endogenous RNA subset are encoded by a plurality of distinct genes; and (g) comparing the identified RNAs of step f) with the RNAs from a control RNA subset, and optionally the levels of one or more RNAs in step f) to the levels of the one or more RNAs in the control RNA subset, from the mRNP complex generated by performing steps b-f on a control cell, wherein the control cell is of the same type as the test cell and is not exposed to the test compound;

thereby evaluating the effect of the test compound on the identity, and optionally the quantity, of the endogenous RNA subset.

15. The method of claim 14, wherein the ligand is an RBP.

16. The method of claim 15, wherein the RBP is ELAV/Hu protein.

17. The method of claim 15, wherein the RBP is HuA or HuB.

18. The method of claim 15, wherein the test compound is a drug.

19. The method of claim 14, wherein the epitope-tagged ligand comprises an RAP.

20. The method of claim 14, wherein the cell is a diseased cell.

21. The method of claim 20, wherein the diseased cell is a tumor cell.

22. The method of claim 20, wherein the diseased cell is a cell infected with a pathogen.

23. The method of claim 14, wherein the control cell is a diseased cell.

24. The method of claim 20, wherein the test compound is a drug used in the treatment of the diseased cell.

25. The method of claim 14, wherein the test compound is a drug.

26. The method of claim 14, wherein the control cell is a non-diseased cell.

27. The method of claim 14, wherein the step of identifying in step f) further comprising comprises determining amounts of the endogenous proteins in the RNP complex.

28. The method of claim 14, wherein the endogenous RNA subset is identified en masse.

\* \* \* \* \*

SEQUENCE LISTING

```
<160> NUMBER OF SEQ ID NOS: 38

<210> SEQ ID NO 1
<211> LENGTH: 37
<212> TYPE: RNA
<213> ORGANISM: Artificial Sequence
<220> FEATURE:
<223> OTHER INFORMATION: 3'-UTR consensus sequence of CD44

<400> SEQUENCE: 1
auuuucuauu ccuuuuuuau uuuaugucau uuuuuua                                37

<210> SEQ ID NO 2
<211> LENGTH: 30
<212> TYPE: RNA
<213> ORGANISM: Artificial Sequence
<220> FEATURE:
<223> OTHER INFORMATION: 3'-UTR consensus sequence of IGF-2

<400> SEQUENCE: 2
uaaaaaacca aauuugauug gcucuaaaca                                        30

<210> SEQ ID NO 3
<211> LENGTH: 27
<212> TYPE: RNA
<213> ORGANISM: Artificial Sequence
<220> FEATURE:
<223> OTHER INFORMATION: 3'-UTR consensus sequence of IGF-2

<400> SEQUENCE: 3
uaaagaaauu aauuggcuaa aaacaua                                           27

<210> SEQ ID NO 4
<211> LENGTH: 23
<212> TYPE: RNA
<213> ORGANISM: Artificial Sequence
```

```
<220> FEATURE:
<223> OTHER INFORMATION: 3'-UTR consensus sequence of IGF-2

<400> SEQUENCE: 4
cuaaaaauua auuggcuuaa aaa                                            23

<210> SEQ ID NO 5
<211> LENGTH: 17
<212> TYPE: RNA
<213> ORGANISM: Artificial Sequence
<220> FEATURE:
<223> OTHER INFORMATION: 3'-UTR consensus sequence of HOX 2.5

<400> SEQUENCE: 5
ucacucuuau uauuuau                                                   17

<210> SEQ ID NO 6
<211> LENGTH: 16
<212> TYPE: RNA
<213> ORGANISM: Artificial Sequence
<220> FEATURE:
<223> OTHER INFORMATION: 3'-UTR consensus sequence of HOX 2.5

<400> SEQUENCE: 6
aaauuuuauu aaguua                                                    16

<210> SEQ ID NO 7
<211> LENGTH: 20
<212> TYPE: RNA
<213> ORGANISM: Artificial Sequence
<220> FEATURE:
<223> OTHER INFORMATION: 3'-UTR consensus sequence of HOX 2.5

<400> SEQUENCE: 7
aucagguuca uuuugguugu                                                20

<210> SEQ ID NO 8
<211> LENGTH: 13
<212> TYPE: RNA
<213> ORGANISM: Artificial Sequence
<220> FEATURE:
<223> OTHER INFORMATION: 3'-UTR consensus sequence of Inhibitor J6

<400> SEQUENCE: 8
auuuuaucug uua                                                       13

<210> SEQ ID NO 9
<211> LENGTH: 33
<212> TYPE: RNA
<213> ORGANISM: Artificial Sequence
<220> FEATURE:
<223> OTHER INFORMATION: 3'-UTR consensus sequence of Inhibitor J6

<400> SEQUENCE: 9
uuuuguuuuu cucccuuuuu uaguuuuuuc aaa                                 33

<210> SEQ ID NO 10
<211> LENGTH: 32
<212> TYPE: RNA
<213> ORGANISM: Artificial Sequence
<220> FEATURE:
<223> OTHER INFORMATION: 3'-UTR consensus sequence of GADD45

<400> SEQUENCE: 10
uauuuuuuuu cuuuuuuuuu uuuggucuuu au                                  32
```

```
<210> SEQ ID NO 11
<211> LENGTH: 31
<212> TYPE: RNA
<213> ORGANISM: Artificial Sequence
<220> FEATURE:
<223> OTHER INFORMATION: 3'-UTR consensus sequence of GADD45

<400> SEQUENCE: 11
uuaaauucuc agaaguuuua uuauaaaucu u                                    31

<210> SEQ ID NO 12
<211> LENGTH: 36
<212> TYPE: RNA
<213> ORGANISM: Artificial Sequence
<220> FEATURE:
<223> OTHER INFORMATION: 3'-UTR consensus sequence of Nexin 1

<400> SEQUENCE: 12
uucuguuaaa uauuuuaua uacugcuuuc uuuuuu                                36

<210> SEQ ID NO 13
<211> LENGTH: 33
<212> TYPE: RNA
<213> ORGANISM: Artificial Sequence
<220> FEATURE:
<223> OTHER INFORMATION: 3'-UTR consensus sequence of Nexin 1

<400> SEQUENCE: 13
auuuuauagu aguuuuaug uuuuuaugga aaa                                   33

<210> SEQ ID NO 14
<211> LENGTH: 22
<212> TYPE: RNA
<213> ORGANISM: Artificial Sequence
<220> FEATURE:
<223> OTHER INFORMATION: 3'-UTR consensus sequence of Nexin 1

<400> SEQUENCE: 14
auuugccuuu uuaauucuuu uu                                              22

<210> SEQ ID NO 15
<211> LENGTH: 30
<212> TYPE: RNA
<213> ORGANISM: Artificial Sequence
<220> FEATURE:
<223> OTHER INFORMATION: 3'-UTR consensus sequence of Egr-1

<400> SEQUENCE: 15
uauuuugugg uuuuauuuua cuuuguacuu                                      30

<210> SEQ ID NO 16
<211> LENGTH: 13
<212> TYPE: RNA
<213> ORGANISM: Artificial Sequence
<220> FEATURE:
<223> OTHER INFORMATION: 3'-UTR consensus sequence of Zif 268

<400> SEQUENCE: 16
uuuuguuuuc cuu                                                        13

<210> SEQ ID NO 17
<211> LENGTH: 22
<212> TYPE: RNA
<213> ORGANISM: Artificial Sequence
<220> FEATURE:
<223> OTHER INFORMATION: 3'-UTR consensus sequence of Neuronal-Cadherin
```

<400> SEQUENCE: 17
uuuuuuauuu ucuguauuuu uu                                          22

<210> SEQ ID NO 18
<211> LENGTH: 29
<212> TYPE: RNA
<213> ORGANISM: Artificial Sequence
<220> FEATURE:
<223> OTHER INFORMATION: 3'-UTR consensus sequence of Neuronal-Cadherin

<400> SEQUENCE: 18
uuuuuuuuaa auuuuuuau uuucuuuuu                                    29

<210> SEQ ID NO 19
<211> LENGTH: 22
<212> TYPE: RNA
<213> ORGANISM: Artificial Sequence
<220> FEATURE:
<223> OTHER INFORMATION: 3'-UTR consensus sequence of Neuronal-Cadherin

<400> SEQUENCE: 19
uuuuuuauuu ucuguauuuu uu                                          22

<210> SEQ ID NO 20
<211> LENGTH: 23
<212> TYPE: RNA
<213> ORGANISM: Artificial Sequence
<220> FEATURE:
<223> OTHER INFORMATION: 3'-UTR consensus sequence of Neuronal-Cadherin

<400> SEQUENCE: 20
uuuuuaauuu uuuaauuuuu uuu                                         23

<210> SEQ ID NO 21
<211> LENGTH: 19
<212> TYPE: RNA
<213> ORGANISM: Artificial Sequence
<220> FEATURE:
<223> OTHER INFORMATION: 3'-UTR consensus sequence of integrin alpha 5

<400> SEQUENCE: 21
aaugguuuau auuuaugau                                              19

<210> SEQ ID NO 22
<211> LENGTH: 17
<212> TYPE: RNA
<213> ORGANISM: Artificial Sequence
<220> FEATURE:
<223> OTHER INFORMATION: 3'-UTR consensus sequence of integrin alpha 5

<400> SEQUENCE: 22
uuguuuauau cuucaau                                                17

<210> SEQ ID NO 23
<211> LENGTH: 16
<212> TYPE: RNA
<213> ORGANISM: Artificial Sequence
<220> FEATURE:
<223> OTHER INFORMATION: 3'-UTR consensus sequence of SEF2
<220> FEATURE:
<221> NAME/KEY: misc_feature
<222> LOCATION: (14)..(14)
<223> OTHER INFORMATION: wherein n at position 14 is a U, G, C or A

<400> SEQUENCE: 23
uucaagcgcu uganuu                                                 16

```
<210> SEQ ID NO 24
<211> LENGTH: 25
<212> TYPE: RNA
<213> ORGANISM: Artificial Sequence
<220> FEATURE:
<223> OTHER INFORMATION: 3'-UTR consensus sequence of Cf2r

<400> SEQUENCE: 24
ugcaucgauc cguugauuua cuacu                                              25

<210> SEQ ID NO 25
<211> LENGTH: 26
<212> TYPE: RNA
<213> ORGANISM: Artificial Sequence
<220> FEATURE:
<223> OTHER INFORMATION: 3'-UTR consensus sequence of integrin beta

<400> SEQUENCE: 25
uauaauuuuu aauuuuuuau uauuuu                                             26

<210> SEQ ID NO 26
<211> LENGTH: 36
<212> TYPE: RNA
<213> ORGANISM: Artificial Sequence
<220> FEATURE:
<223> OTHER INFORMATION: 3'-UTR consensus sequence of integrin beta

<400> SEQUENCE: 26
uuauuuuacc uuuuuuuuuu uucuuuaauu ccuggu                                  36

<210> SEQ ID NO 27
<211> LENGTH: 19
<212> TYPE: RNA
<213> ORGANISM: Artificial Sequence
<220> FEATURE:
<223> OTHER INFORMATION: 3'-UTR consensus sequence of CTCF

<400> SEQUENCE: 27
uuaugaaugu uauauuugu                                                     19

<210> SEQ ID NO 28
<211> LENGTH: 27
<212> TYPE: RNA
<213> ORGANISM: Artificial Sequence
<220> FEATURE:
<223> OTHER INFORMATION: 3'-UTR consensus sequence of CTCF

<400> SEQUENCE: 28
ucuuaauuuu uucucuuuuu uuucuuu                                            27

<210> SEQ ID NO 29
<211> LENGTH: 33
<212> TYPE: RNA
<213> ORGANISM: Artificial Sequence
<220> FEATURE:
<223> OTHER INFORMATION: 3'-UTR consensus sequence of TGF beta 2

<400> SEQUENCE: 29
uuuuuuuuuc cuuuuaauug uaaaugguuc uuu                                     33

<210> SEQ ID NO 30
<211> LENGTH: 37
<212> TYPE: RNA
<213> ORGANISM: Artificial Sequence
<220> FEATURE:
<223> OTHER INFORMATION: 3'-UTR consensus sequence of TGF beta 2
```

```
<400> SEQUENCE: 30
uuaaugauca uucagauugu auauauuugu uuccuuu                                    37

<210> SEQ ID NO 31
<211> LENGTH: 25
<212> TYPE: RNA
<213> ORGANISM: Artificial Sequence
<220> FEATURE:
<223> OTHER INFORMATION: 3'-UTR consensus sequence of TGF beta 2

<400> SEQUENCE: 31
uucaauuuuu uuuauauacu aucuu                                                 25

<210> SEQ ID NO 32
<211> LENGTH: 22
<212> TYPE: RNA
<213> ORGANISM: Artificial Sequence
<220> FEATURE:
<223> OTHER INFORMATION: 3'-UTR consensus sequence of TGF beta 2

<400> SEQUENCE: 32
uuuuucuuua auugguuuuu uu                                                    22

<210> SEQ ID NO 33
<211> LENGTH: 27
<212> TYPE: RNA
<213> ORGANISM: Artificial Sequence
<220> FEATURE:
<223> OTHER INFORMATION: 3'-UTR consensus sequence of MTP

<400> SEQUENCE: 33
ugucuugucu gagcauuuau uuucaaa                                               27

<210> SEQ ID NO 34
<211> LENGTH: 23
<212> TYPE: RNA
<213> ORGANISM: Artificial Sequence
<220> FEATURE:
<223> OTHER INFORMATION: 3'-UTR consensus sequence of MTP

<400> SEQUENCE: 34
uucucgucuu guuuauuuua caa                                                   23

<210> SEQ ID NO 35
<211> LENGTH: 32
<212> TYPE: RNA
<213> ORGANISM: Artificial Sequence
<220> FEATURE:
<223> OTHER INFORMATION: 3'-UTR consensus sequence of MTP

<400> SEQUENCE: 35
uauaauaaua guuuauguuu uggauguuug gu                                         32

<210> SEQ ID NO 36
<211> LENGTH: 27
<212> TYPE: RNA
<213> ORGANISM: Artificial Sequence
<220> FEATURE:
<223> OTHER INFORMATION: 3'-UTR consensus sequence of cyclin D2

<400> SEQUENCE: 36
augucuuguu cuuuguguuu uuaggau                                               27
```

```
<210> SEQ ID NO 37
<211> LENGTH: 11
<212> TYPE: RNA
<213> ORGANISM: Artificial Sequence
<220> FEATURE:
<223> OTHER INFORMATION: in vitro consensus sequence
<220> FEATURE:
<221> NAME/KEY: misc_feature
<222> LOCATION: (1)..(2)
<223> OTHER INFORMATION: nn is AU or GA
<220> FEATURE:
<221> NAME/KEY: misc_feature
<222> LOCATION: (10)..(11)
<223> OTHER INFORMATION: nn is UA or AG

<400> SEQUENCE: 37
nnuuuauuun n                                                         11

<210> SEQ ID NO 38
<211> LENGTH: 7
<212> TYPE: RNA
<213> ORGANISM: Artificial Sequence
<220> FEATURE:
<223> OTHER INFORMATION: in vitro binding sequence for HuB

<400> SEQUENCE: 38 uuuauuu                                                               7
```